(12) United States Patent
Sankaranarayanan

(10) Patent No.: US 7,223,777 B2
(45) Date of Patent: May 29, 2007

(54) COMPOUNDS FOR THE MANAGEMENT OF AGING-RELATED AND DIABETIC VASCULAR COMPLICATIONS, PROCESS FOR THEIR PREPARATION, THERAPEUTIC AND COSMETIC USES THEREOF

(75) Inventor: Alangudi Sankaranarayanan, Ahmedabad (IN)

(73) Assignee: Torrent Pharmaceuticals Ltd., Gujarat (IN)

( * ) Notice: Subject to any disclaimer, the term of this patent is extended or adjusted under 35 U.S.C. 154(b) by 0 days.

(21) Appl. No.: 10/116,135

(22) Filed: Apr. 5, 2002

(65) Prior Publication Data

US 2003/0045554 A1 Mar. 6, 2003

Related U.S. Application Data

(60) Provisional application No. 60/281,380, filed on Apr. 5, 2001.

(51) Int. Cl.
*A61K 31/4439* (2006.01)
*C07D 401/04* (2006.01)

(52) U.S. Cl. .................. 514/341; 546/275.4; 546/276.1
(58) Field of Classification Search ............ 546/275.4, 546/276.1; 514/341
See application file for complete search history.

(56) References Cited

U.S. PATENT DOCUMENTS

| 4,758,583 A | 7/1988 | Cerami et al. ............... 514/399 |
| 5,137,916 A | 8/1992 | Ulrich et al. ................ 514/535 |
| 5,272,176 A | 12/1993 | Ulrich et al. ................ 514/535 |
| 5,514,676 A | 5/1996 | Ulrich et al. ............. 514/231.2 |
| 5,656,261 A | 8/1997 | Cerami et al. ................. 424/53 |
| 5,853,703 A | 12/1998 | Cerami et al. ................. 424/53 |
| 2001/0025056 A1 | 9/2001 | Maignan ...................... 514/733 |

FOREIGN PATENT DOCUMENTS

| EP | 0339496 A2 | 11/1989 |
| EP | 0 563 686 A1 | 10/1993 |
| EP | 1068864 A1 | 1/2001 |
| EP | 1110539 A1 | 6/2001 |
| WO | WO 00/66101 | 11/2000 |
| WO | WO 01/25208 A1 | 4/2001 |
| WO | WO 01/25209 A1 | 4/2001 |

OTHER PUBLICATIONS

Ferles et al, "Studies in the pyridine , etc" CA 96: 104035 (1982).*
Brownlee M et al. Science, 1986, 232: 1629-1632.
Vasan et al., Nature 1996; 382: 275-278.
Beisswenger P. J et al., Diabetes vol. 11, Jul. ; 824-829.
Makita et al., The New England Journal of Medicine, vol. 325 No. 12, Sep. 19, 1991, 836-842.
Yamauchi A et al., diabetes Res Clin Pract Jan. 1997 34(3) : 127-33 (Abstract).
Ellis E N et al., Metabolism Oct. 1991; 40(10): 1016-1019(Abstract).
Soulis Liparoto et al., Diabetes 40: 1328-34, 1991.
Hirata C et al., Biochem Biophys Res Commun Jul. 30, 1997: 236(3); 712-715.
Murata et al., Diabetologia Jul. 1997; 40(7) : 764-769.
Hammes et al. Proc. Natl. Acad Sci USA, vol. 88 pp. 11555-11558, Dec. 1991, Medical Sciences.
Roufail E. Diabetologia Dec. 1998; 41 (12): 1419-1425.
Kihara Mikihiro et al. Proc. Natl. Acad. Sci. U.S.A, vol. 88, pp. 6107-6111, Jul. 1991, Medical Sciences.
Miyauchi Y et al, Eur J Endocrinol Apr. 1996: 134(4): 467-73(Abstract).
Yagihashi Soroku et al. Diabetes vol. 41, Jan. 1992, 47-52.
Bucala R, Diabetes Res Clin Pract Feb. 1996: 30 Suppl: 123-30(Abstract).
Kirstein. M et al, Proc. Natl. Acad. Sci. U.S.A vol. 87, pp. 9010-9014 Nov. 1990, Medical Sciences.
Wolffenbuttel Bruce H R et al., Proc. Natl. Acad. Sci. USA, vol. 95, pp. 4630-4634, Apr. 1998, Medical Sciences.
Aronson D et al., J Am Coll Cardiol Mar. 1, 1996; 27(3): 528-35, (Abstract).
Seftel AD, Urology, Dec. 1997: 50(6): 1016-26.
Michael P. Vitek et al., Proc. Natl. Acad, Sci USA, vol. 91, pp. 4766-4770, May 1994 Neurobiology.
Yong Ming Li et al., Proc. Natl. Acad. Sci. USA, vol. 93,pp. 3902-3907, Apr. 1996, Medical Sciences.

(Continued)

*Primary Examiner*—Patricia L. Morris
(74) *Attorney, Agent, or Firm*—Sughrue Mion, PLLC

(57) ABSTRACT

The invention discloses a new clause of a five membered heterocylic ring compounds of general formula I

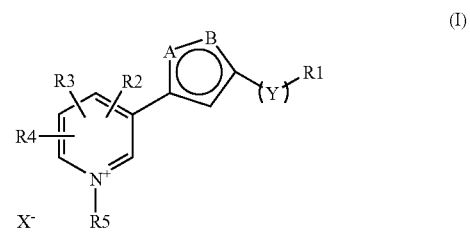

and its pharmaceutically or cosmetically acceptable salts, wherein R1, R2, R3, R4, R5, A, B, X and Y are as defined in the specification. The invention also discloses a process for preparation of these compound and their therapeutic and cosmetic applications particularly in the management of aging related and diabetic vascular complications. The compounds in question act by triple action of an AGE (Advanced Glycation Endproducts) breaker, AGE inhibitor and free radical scavenger which make them most suitable in different therapeutic and cosmetic applications. The invention also discloses pharmaceuticals and cosmetic compositions comprising these compounds and method of treatment of diseases caused by accumulation of AGE and/or free radicals in the body cells.

15 Claims, No Drawings

OTHER PUBLICATIONS

Hakon Nordbo, J Dent Res 58(4): 1429, Apr. 1979, (Abstract).
Boni R, et al. Schweiz Med Wochenschr(2000), Sep. 9; 130(36) : 1272-8 (Abstract).
Odetti P et al., Gerontology(1998) ; 44(4) : 187-91(Abstract).
Pugliese PT,Dermatol Nurs Dec. 1998 10(6) : 401-16; 187-91quiz 417-18 (Abstract).
Calabrese V et al., Drugs Exp Clin. Res X X V (6) 281-287 (1999).
Berneburg M et al., Photodermatol photoimmunol Photomed (2000) Dec. ; 16(6) ; 239-44 (Abstract).
Masaki H, Biochem Biophys Res Commun Jun. 18, 1997, 235(2): 306-10 (Abstract).
Hitoshi Masaki et. al., Biochemia et Biophysica Acta 1428 (1999) 45-56.
G. Muinch et al., J Neural Transm (1998) 105 : 439-461.
Smith M A et al., Biochim Biophys Acta Jul. 26, 2000; 1502(1):139-44, (Abstract).
Browne S.E et al., Brain Pathology 9 : 147-163 (1999).
E.J Harper, The 24$^{th}$ annual Waltham / OSU symposium, (2000).
Dario Giugliano et al., Diabetes Care, vol. 19, No. 3, Mar. 1996, 257-267.
Ishii Hiromasa et al., Journal of Gastroenterology and Hepatology (1997) 12 (Suppl.), S272-S282.
G. Zalba et al., J Physiol Biochem, 56 (1), 57-64, 2000.
Crawford R.S et al., Arterioscler Thromb Vasc Biol Sep. 1998;18 (9): 1506-13, (Abstract).
Maxwell et al., Br j Clin Pharmacol 1997 :44: 307-317.
MacNee W et al., Trends Mol Med Feb. 2001; 7(2): 55-62(Abstract).
Brownlee, Annu. Review Med. , 223-233(1995).
C. Jeanmaire et al., British Journal of Dermatology 2001 : 145: 10-18.
Hammes H P et al. , Diabetologia Jan. 1994 ; 37(1):32-35.
Tupper, D. E. et al.: "The synthesis and Reaction of 4-(2-and3-Thienyl)-tetrahydroisoquinolines" J. Heterocyclic Chem, vol. 33, No. 4, 1996, pp. 1123-1129.
Westphal, O. et al.; "Synthesis of New Thiazolo -[3,2-α] pyridinium Salts" Angew.Chem., vol. 8, No. 1, 1969, p. 74.

* cited by examiner

COMPOUNDS FOR THE MANAGEMENT OF AGING-RELATED AND DIABETIC VASCULAR COMPLICATIONS, PROCESS FOR THEIR PREPARATION, THERAPEUTIC AND COSMETIC USES THEREOF

CROSS REFERENCE TO RELATED APPLICATIONS

This application claims benefit from U.S. provisional application No. 60/281,380 filed Apr. 5, 2001 which is incorporated herein by reference in its entirety.

BACKGROUND OF THE INVENTION

1. Field of the Invention

The present invention relates to a new class of compounds of five membered heterocyclic ring compounds and to their use in treatment of diabetes and related illnesses. More particularly the invention relates to compounds of this series, methods for their preparation, pharmaceutical composition containing these compounds and their use in the treatment of complications of diabetes mellitus. The compounds of this series exhibit AGE breaking and inhibiting activity, which is essential for the treatment of diabetic and aging-related vascular and neurovascular complications including kidney disease, nerve damage, atherosclerosis, retinopathy, inflammatory disorders, immunological disorders, oxidative stress and dermatological & cosmetic indications.

The invention also extends to the method of reversing the discoloration of teeth resulting from nonenzymatic browning in the oral cavity by administration of an effective amount of these compounds to reverse preformed advanced glycosylation crosslinks.

These compounds, also exhibit free radical scavenging activity and hence are useful in the treatment of diseases caused by free radicals besides their cosmetic applications The triple function of a free radical scavenger, AGE breaker and AGE inhibitor of these compounds can be effectively used in cosmetic compositions which are capable of arresting and reversing the process of skin aging resulting from an increased accumulation of advanced glycation endproducts (AGEs) on the skin proteins and photo damage through free radical actions. The invention further relates to composition and method for scavenging free-radicals from the body cells.

2. Description of the Related Art

Maillard in 1912 found that reducing sugars, such as glucose and ribose react with proteins to form brown pigments. Further studies have shown that this is an irreversible non-enzymatic reaction, which occurs in several natural systems including stored foodstuff. Maillard reaction occurs in two stages, early and advanced. Initially, proteins react with glucose to form stable Amadori products, which subsequently cross-links to form advanced glycation end products (AGE). In most cases, the formation of AGE also accompanies browning of the proteins and increase in the fluorescence.

In diabetes, where blood glucose level is significantly higher than normal, the reaction of glucose with several proteins such as hemoglobin, lens crystallin and collagen, gives rise to the formation of AGE, which in turn, is responsible for the complications associated with diabetes, such as nephropathy, microangiopathy, endothelial dysfunction and other organ dysfunctions. In addition, the activity of several growth factors, such as basic fibroblast growth factor, is also impaired, AGE products, unlike normal proteins in tissue, have a slower rate of turnover and replenishment. It has been reported that AGE products may in fact elicit a complex immunological reaction involving RAGE (Receptor for Advanced Glycation End Products) receptors and activation of several incompletely defined immunological processes. It has been documented that diabetes with evidence of microangiopathy and macroangiopathy also show evidence of oxidative stress, the mechanism of which has not been elucidated.

In vitro AGE formation can be studied in the laboratory by incubating reducing sugars, such as ribose or glucose with bovine serum albumin. AGE formation can be detected by increase in the fluorescence or increased cross reactivity with anti-AGE antibodies. The increase in fluorescence seems to precede formation of AGE specific antigenic epitopes. This increase in fluorescence is used to monitor the increased AGE formation in vitro (Brownlee M et al, Science 1986; 232:1629–1632). In addition to the increase in the fluorescence, one of the most important features of in vitro AGE formation is the formation of antigenic epitopes that are specific to AGE and not to the native proteins. Therefore, it is possible to raise antibodies against advanced glycation end products of one protein and use them to detect AGE formation in other proteins. This has served as an important analytical tool in AGE research.

Due to the clinical significance of AGE formation, many approaches are being used to diagnose, prevent, or revert AGE formation in the body. The formation of AGE could be inhibited by reacting with an early glycosylation product that results from the original reaction between the target protein and glucose. The inhibition was believed to take place as the reaction between the inhibitor and the early glycosylation product appeared to interrupt the subsequent reaction of the glycosylated protein with additional protein material to form the cross linked late stage product. Compounds like aminoguanidine act to inhibit AGE formation by such mechanism.

The formation of AGE on long-lived proteins is also associated with cross-linking of these proteins. The AGE derived protein cross-links have been shown to be cleaved by compounds like N-phenacyl thiazolium bromide (PTB), which reacts with and cleaves covalent, AGE derived protein cross links (Vasan et al. Nature 1996; 382: 275–278 ; U.S. Pat. No. 5,853,703, Date of Patent: Dec. 29, 1998). The mechanism of reducing the AGE content in tissues is expected to take place relatively rapidly, in contrast to aminoguanidine, which acts slowly by its very nature of mechanism of action.

The compounds which are AGE breaker or AGE inhibitor are of prime importance in therapeutic applications as mentioned below:

AGE Breakers:

The compounds which can break the accumulated AGE can be used as a medicament in the treatment of diabetic complications and aging-related diseases caused by accumulation of AGE.

The compounds which can inhibit accumulation of AGE by breaking AGE, can be used as a medicament for arresting the aggravation of diseases such as diabetes and aging related complications caused by accumulation of AGE.

AGE Inhibitors:

The compounds which can inhibit accumulation of AGE by inhibiting formation of AGE, can be used in a medica ment for the diseases such as diabetes and aging related complications caused by accumulation of AGE.

The unchecked formation of AGE in vivo, such as in diabetics related diseases, can lead to severe physiological impairment. For example, in diabetic neuropathy and retinopathy, the functional integrity of the capillary wall barrier and inner blood retinal barrier, respectively, are defective, as evidenced by the abnormal attachment of the endothelium to the basement membrane. This defect is a direct consequence of the cross-linking of structural proteins by glycation. The etiology of diabetic neurovascular disorders, as well as immunological disorders, is the formation of AGE. Currently, it is believed that inhibiting AGE formation, or the breaking of existing AGE, would be beneficial in a variety of diseases, including nephropathy, neuropathy, arteriosclerosis, and dermatological disorders.

Studies have demonstrated positive effects of agents that break AGE, such as in studies on cardiovascular complications related to aging, a condition which is accelerated in experimental diabetic conditions (Wolffenbuttel et al., 1998).

In another pharmacological approach to controlling levels of AGE in tissues, especially in those tissues in which AGE has already accumulated to levels which are responsible for sub-clinical or clinical pathology, administration of agents that reverse or break AGE has proven successful. As described in U.S. Pat. Nos. 5,656,261 and 5,853,703 agents and methods are disclosed which reverse (or cleave or break) AGE formation in vitro and in vivo.

Several successful therapeutic approaches have also been achieved based upon blocking the accumulation of AGE in vivo. One approach, exemplified in U.S. Pat. No. 4,758,583 concerns the inhibition of the formation of AGE from its precursors, by the administration of agents such as aminoguanidine and related compounds.

As has been shown in the above-cited references, compounds which block AGE formation, or break AGE, are reasonably correlated to the treatment of AGE-related disorders, such as diabetic nephropathy, neuropathy, retinopathy, and arteriosclerosis, dermatological disorders, non-enzymatic browning of the oral cavity, endothelial or other organ dysfunction and growth impairment.

The correlation between the onset of AGE with various diseases has also been described in various literature as discussed below.

The correlation between the formation of Advanced Glycation End products (AGE) and nephropathy is well established by several research publications. Beisswenger (1995) has shown that AGE concentration in human diabetic subjects correlates with early manifestation of renal diseases. Makita et al (1991) has shown that increase in AGE peptides parallels with the severity of renal dysfunction. The above citations clearly show that AGE is the principal cause of diabetic nephropathy. Yamauchi (1997) showed that prevention of AGE formation by aminoguanidine inhibits development of diabetic nephropathy. Aminoguanidine administration is also shown to ameliorate thickening of glomerular basement membrane of diabetic rats (Ellis 1991). Aminoguanidine is also shown to attenuate the rise in albuminuria in experimental diabetic rats (Soulis-Liparota, 1991).

AGE is also shown to induce expression of vascular endothelial growth factor in retinal muller cells (Hirata, 1997, Murata, 1997) and therefore may promote intraocular neovascularization in diabetic retinopathy. Aminoguanidine treatment is shown to retard progression of diabetic retinopathy in rat model (Hammes, 1991, Hammes, 1994, Roufail, 1998).

Aminoguanidine treatment is also shown to improve nerve conduction velocity in diabetic rats (Kihara, 1991 Miyauchi, 1996 and Yagihashi, 1992).

Bucala (1996) has extensively reviewed various aspects of development of Atheroscelrosis and stated that accumulation of AGE can trigger a series of cellular events, such as cellular oxidative stress, expression of adhesion molecules, endothelial transmigration of monocytes, etc. and these events can lead to atherosclerosis. Kirstein (1990) have demonstrated that (i) in vitro and in vivo-formed AGE proteins are chemotactic for human blood monocytes, (ii) sub-endothelial AGE can induce monocyte migration across intact endothelium and (iii) interaction of monocyte with AGE containing matrix results into induction platelet derived growth factor.

Thus, it can be concluded that AGE, upon interaction with endothelial cells through its receptor RAGE, activate nuclear factor Kappa B and induce various genes expressing adhesion molecules. AGE-endothelium interactions also increase oxidative stress, initiate monocyte migration, block endothelial nitric oxide and stimulate angiogenesis. All these conditions result in conditions such as atherosclerosis.

Other dysfunctions demanding lower tissue AGE burden include, Hypertension, Restenosis, abnormal tissue hindrance in peritoneal dialysis, Erectile Dysfunction and Alzheimer disease. Similarly, on the other hand, non-enzymatic cross-linking of structural proteins, such as collagen, leads to increased stiffness of arteries and reduce arterial compliance and distensibility. In fact, treatment of AGE-breaker ALT-711 is shown to reverse diabetes induced increase of arterial stiffness and improve arterial compliance (Wolffenbuttel 1998). Aronson et al (1996) have reviewed role of AGE in promoting inflammatory cell recruitment and smooth muscle proliferation and suggested it to be a likely reason for greater restenosis, abnormal tissue hindrance in peritoneal dialysis rate in diabetic patients.

Seftel (1997) has shown significant elevation of pentosidine in the penile tissue of diabetic patients as compared to non-diabetic. They have speculated a mechanism for AGE mediated erectile dysfunction via upregulation of inducible nitric oxide and downregulation of endothelial nitric oxide in penile tissues.

Vitek et al (1994) have reported that beta amyloid peptides (βAP) aggregate slowly under normal physiological conditions whereas AGE modified (βAP) showed a much more rapid aggregation. Plaque numbers increase in association with neuronal degeneration and cognitive decline in AD. Aggregated but not monomeric βAP is actively neurotoxic. Hence interference with the process by which AGE formation enhances βAP aggregation or inhibition of AGE formation or AGE breaker therapy will provide new therapeutic opportunities to reduce the pathophysiological changes associated with Alzheimer's disease.

Hence AGE inhibitors/breakers would be beneficial in reducing the aggregation of βAP, leading to the prevention/treatment of Alzheimer's disease.

Li et al (1996) have provided evidence for an interrelationship between two key manifestations of physiological aging in the rat cardiovascular and renal decline and the spontaneous age associated biochemical process termed advanced glycation thought to contribute to progressive tissue damage and organ failure. In their study aminoguanidine (an AGE inhibitor) was found to significantly prevent tissue damage as a result of inhibiting AGE formation. Lower tissue AGE burden in rats as a result of aminoguanidine administration was found to preserve an altogether more satisfactory level of cardiovascular and renal function as evidenced by the generally healthier appearance of old rats treated by aminoguanidine as compared to the untreated age and weight matched controls. Hence AGE inhibitors could be used for the prevention of aging related disorders.

The nonenzymatic browning reaction, which occurs in the oral cavity, results in the discoloration of teeth. Anti-plaque agents such as chlorhexidine have been reported to accelerate the non-enzymatic browning reaction and further the staining of teeth. (Nordbo, J. Dent. Res., 58, p. 1429 (1979)). Nordbo has proposed that chlorhexidine results in tooth staining in two ways: first, by increasing the formation of pelicle which contains more amino groups, and secondly, by catalysis of the Maillard reaction leading to colored products.

The ability of inhibitors of non-enzymatic browning reaction to prevent the discoloration of protein on a surface, such as that which occurs on the tooth surface has been demonstrated with in vitro experiments in U.S. Pat. No. 5,137,916; U.S. Pat. No. 5,272,176.

Compounds that have the ability to inhibit or reverse AGE have been claimed to be useful for the inhibiting or reversing the discoloration of teeth resulting from non-enzymatic browning in the oral cavity. (U.S. Pat. Nos. 5,272,176; 5,853,703)

All these evidences point out to a common underlying mechanism for the pathophysiological conditions associated with diabetes and that is the formation of Advanced Glycation Endproducts. As the total tissue burden of AGE increases, the severity of the pathological symptoms too increase. On the other hand, if the quantum of AGE is controlled by the compounds like Aminoguanidine, the progression of disease is also retarded. In the present invention, the inhibition of Advanced Glycation Endproducts is described.

Renal disease is a leading cause of death and diability in diabetes. Chronic dialysis and renal transplantation are quite routine in patients with renal failure due to diabetes. Peritoneal Dialysis (PD) works on the same principle as hemodialysis, but the blood is cleaned while inside the body rather than through a machine. The major difference in peritoneal dialysate formulations as compared to hemodialysis in the amount of higher glucose concentrations used as an osmotic agent (1.5, 2.5 or 4.25 g/dL). High glucose formation in humans is associated with the progressive formation of Advanced Glycosylation End-products (AGE's) that damage organ function. AGE's contribute to the development of abnormal fibrous tissue and reduces the ability of the peritoneum to filter fluids, leading to a failure of the PD procedure.

The compounds which can alter the AGE contents of the tissue could be used to prevent this process and other medical complications arising from the formation of AGE's. Use of an AGE breaker or inhibitor in the dialysis fluid would inhibit formation of abnormal fibrous tissue and thereby facilitate peritoneal dialysis proceduce. Accordingly the compound of the invention can be used for preparation of dialysis fluid for peritoneal dialysis of a diabetic patient.

Reducing the tissue burden of AGE is expected to reverse these conditions, whereas preventing accumulation up to critical mass could prevent the condition from occurring. These conditions are listed bellow:

a. vascular and neuro-vascular complications,
b. nephrological disorder,
c. neurological disorder,
d. atherosclerosis,
e. retinal disorder,
f. dermatological disorder,
g. non-enzymatic browning of oral cavity,
h. endothelial or other organ dysfunction,
i. growth impairment,
j. inflammatory disorder,
k. immunological disorder,
l. oxidative stress,
m. aging and diabetic complication,
n. alzheimer disease,
o. restenosis, abnormal tissue hindrance in peritoneal dialysis,
p. abnormal tissue hindrance in peritoneal dialysis and
q. erectile dysfunction.

The compounds showing the activity towards breaking/inhibiting AGE can also be useful for their cosmetic utility.

Health, resilience and youthful appearance of the skin depends, among other things, on several key classes of biological molecules. The key skin molecules are collagen and elastin. Collagen is a protein, forming the structural grid that holds other skin structures. It gives the skin its strength and durability. As any other protein, collagen is composed of amino acids. However it is unusually rich in a few specific amino acids; proline, hydroxy proline, lysine and glycine. Elastin is also a protein, more stretchable than collagen and helps to maintain skin resilience and elasticity. It contains two special amino acids: desmosine and isodesmosine. When both elastin and collagen are at scarce and damaged, the skin looses its shape after being stretched or folded leading to wrinkles and facial sag that happens during the process of aging.

Most modern theories of aging have centered around the notion that age-related deterioration is primarily due to structural and functional modifications of cellular constituents. The currently popular hypothesis are the Free Radical, Glycation or Maillard theories of aging. The first hypothesis proposes that age-related effects are due to free radical reactions that damage cellular constituents. "Free radical" refers to an unstable molecule that has an unpaired or odd electron in an outer orbit, which indiscriminately react with other molecules causing lipid, DNA and protein damage. The latter hypothesis propose that the primary cause of aging is cellular damage resulting from the modification of macromolecules induced by non-enzymatic glycation and Maillard reactions to form advanced glycosylation endproducts (AGEs). Non-enzymatic glycation is the chemical attachment of sugars to protein that eventually causes protein cross linking, which is irreversible. Although these hypothesis were formulated independently, it suggests that free radicals, glycation, and Maillard reactions may in fact represent partially interactive elements of a single, more complex biochemical pathway, and that age-related deterioration is produced by the sum of the damages induced by all three hypotheses, and by their interactions.

Skin, a highly differentiated and complexly structured organ, is particularly vulnerable to free radical damage on exposure to UV radiation resulting in an increased accumulation of AGEs on the skin as well as an increased production of singlet oxygen and super oxide radicals which damage the important skin molecules such as collagen and elastin. Under such situations an anti-oxidative condition through free radical scavenging would certainly enable the skin to maintain its normal resilience and integrity against damage.

Hence, the present invention is directed towards a cosmetic application with an active molecule capable of reversing the AGE cross links and creating an anti-oxidative environment in tissues through its AGE breaking and free radical quenching actions, thereby significantly slowing down the aging manifestations.

The skin is the largest organ in the body, comprising about 15% of the body weight. In terms of chemical composition, the skin is about 70% water, 25% protein and 2% lipids. The remainder includes trace minerals, nucleic acids, glycosoaminoglycans, proteoglycans and numerous other chemicals.

The skin consists of 3 main layers: Epidermis, dermis, subcutaneous tissue. The epidermis is the first barrier between us and the outside world. This layer consists of 3 types of cells; keretinocytes, melanocytes and langerhans cells. The dermis is the middle layer of the skin, the thickest of the skin layers and comprises a tight, sturdy mesh of collagen (type-I and III) and elastin fibers which are the critically important skin proteins. The dermis also consists of fibroblasts, capillaries, lymph nodes, sebaceous glands, sweat glands and hair follicles. The subcutaneous tissue is the innermost layer of the skin comprising mainly of adipocytes, acts as a shock absorber and heat insulator, protecting underlying tissues from cold and mechanical trauma.

Aging is a biological phenomenon which is symbolized by wrinkles and sagging skin. As a person ages, skin cells divide more slowly, and the inner skin, or dermis, starts to thin. Fat cells beneath the dermis begin to atrophy, and the underlying network of elastin and collagen fibers, which provides scaffolding for the surface layers, loosens and unravels. Skin loses its elasticity; when pressed, it no longer springs back to its initial position but instead sags and forms furrows. The skin's ability to retain moisture diminishes; the sweat- and oil-secreting glands atrophy, depriving the skin of their protective water-lipid emulsions. As a consequence, the skin becomes dry and scaly. In addition, the ability of the skin to repair itself diminishes with age, so wounds are slower to heal. Frown lines (those between the eyebrows) and crow's feet (lines that radiate from the corners of the eyes) appear to develop because of pen-permanent small muscle contractions. Habitual facial expressions also form characteristic lines, and gravity exacerbates the situation, contributing to the formation of jowls and drooping eyelids. Since the skin represents the most visible organ of the aging, there is increasing interest in the physiology and reversal of wrinkles, elastoses and senile xerosis. Cutaneous aging is a complex phenomenon consisting of genetically determined intrinsic and extrinsic aging factors(Boni R, Burg G: Schweiz Med Wochenschr (2000) September 9; 130 (36): 1272–8).

Mainly, there are two biologically independent aging processes that occur simultaneously, which account for the major changes seen in skin over time.

1. Extrinsic aging or Photoaging/External Factors and
2. Innate or Intrinsic aging/Internal Factors Extrinsic aging or Photoaging, which results when skin is exposed to the elements like Ultraviolet (UV) radiation, Chemical Pollutants, Allergens, Mechanical damage, etc. Extrinsic aging is primarily caused by ultraviolet radiation of the sun.

Intrinsic aging affects skin by slow, irreversible degeneration of tissue. The factors causing intrinsic aging are genetic, nervous (stresses), immune, hormone disorders and others. Intrinsic aging can be observed over the entire surface of the body, including skin protected from ultraviolet radiation of sun. The phenomenon of glycation as discussed above plays a serious part in intrinsic aging. Proteins from dermis, elastin and collagen react with sugars in the body, especially glucose to result in the binding together of collagen fibers and the synthesis of free radicals. This modifies the structure of the skin causing it to loose its suppleness and become more rigid. Thus, the most noticeable changes on facial skin result from a combination of intrinsic and extrinsic aging processes.

Basically two factors—free radicals and ACE formation are the prominent accelerators of skin wrinkles. The Maillard theory of Skin aging dates back to 1912 when Maillard found that reducing sugars such as glucose and ribose react with proteins to form brown pigments. The Maillard reaction is a series of complex reactions that cause the cross-linking of protein via the interaction of reducing sugars with amino groups of proteins to form stable Amadori products, which subsequently cross-link to form Advanced Glycation End products (AGE). Another property of critical biological significance is the observation that the Amadori products continue to cross-link and polymerize even in the absence of free glucose. Protein crosslink is important since it is responsible for deep wrinkling in the dermis. The formation of AGE crosslinks is also a natural part of the aging and all the processes where protein aging is a serious detriment. During the aging process reducing sugar chemically attaches to the skin's support proteins like elastin and collagen, causing them to become gradually rigid and slowing their renewal. This non-specific and non-enzymatic attachment of the sugar to collagen and elastin lead to the formation of AGE which continues to cross-link and polymerize even in the absence of free glucose. The studies on the role of AGEs in aging collagen using scanning force microscope reveal that in the presence of an increased concentration of AGEs, significant structural alterations have been observed in the collagen fibrils of old rats(Odetti P, Aragno I, et al. Gerontology (1998); 44 (4); 187–91). As a result of this aging process, collagen loses its elasticity and the skin develops wrinkles.

The covalent binding of glucose to the amino group of protein alone is not sufficient to account for structural changes observed in collagen. Oxygen radicals formed during glucose oxidation, and glycated protein oxidation may be involved directly in the formation of AGEs and collagen cross-linking. In vitro studies demonstrate that the presence of oxygen is indispensable for the advanced glycation and cross-linking of collagen. Antioxidative condition and free radical scavengers have been proven to inhibit or slow down the formation of AGEs and the cross-linking of collagen. It is also known that free radical scavengers are essential in protecting the epidermis from damage by free radicals generated both by environmental and endogenous factors (Pugliese P T, Dermatol. Nurs (1998) December: 10 (6): 401–16; quiz 417–18).

Skin, which has a highly differentiated and certainly complex organizational structure, is particularly vulnerable to free radical damage because of its contact with oxygen and other environmental stimuli(Calabrese V, Scapagnini G et. al., Drugs Exp. Clin Res. (1999); 25(6): 281–7). Studies have proved that UV radiation increases the formation of AGEs on collagen, elastin and other skin proteins. It forms a vicious cycle by increasing the accumulation of AGEs on the skin as well as increased production of singlet oxygen and super oxide radicals, which damage the skin protein.

With recent years, substantial progress has been made in unraveling, the underlying mechanisms of photoaging. Induction of matrix metalloproteinases as a consequence of activator protein (AP)-1 and Nuclear factor (NF)—kB activation as well as mutations of mitochondrial DNA have been identified recently(Berneburg M, et. al. Photodermatol Photoimmunol. Photomed (2000) December: 16 (6): 238–44). In the early stage of glycation the condensation of reducing sugars such as glucose with amino groups of proteins generates UVA photo generated singlet oxygen free radicals. It is reported that AGE is an important factor for promoting photoaging in the skin via generation of active oxygen species involving $O_2^-$, $H_2O_2$ and —OH (Masaki H. et. al., Biochem Biophys. Res. Commun (1997) June 18: 235). On the basis of invitro fibroblast studies a possible mechanism is proposed in which AGEs under UVA irradiation generate active oxygen species involving $O_2^-$, $H_2O_2$ and OH while the OH species place a harmful role in promoting cell damage (Hitoshi Masaki et. al. Biochemica et Biophysica Acta 1428 (1999) 45–56). These radicals disrupt the natural balance of the skin by stimulating the skin cells to synthesize metalloproteinases. The metalloproteinase enzymes degrade collagen without synthesizing anti-metalloprotenases that keeps a check on the skin protein degradation, which is a normal biological response. The unbalanced production of metalloproteinase over anti-metalloprotenases induced by singlet oxygen free radicals leads to break down of collagen and elastin of the skin. This is followed by imperfect wound repair of damaged collagenous matrix and accumulation of elastotic material, as a consequence the skin sags and wrinkles.

Due to the exposure of AGEs to UV A radiations, the generation of super oxide anion gets enhanced. This is accomplished through cellular electron transfer chain in which UV A-AGEs energy enhances the passing of electrons onto ground state oxygen. This leads to enhanced formation of super oxide, anion during Adenosine Triphosphate (ATP) synthesis. An enzyme super oxide dismutase converts the super oxide anion into hydrogen peroxide and oxygen. Finally, the catalytic action of iron and copper transforms hydrogen peroxide into toxic hydroxyl radical causes the degradation of skin collagen and elastin which is followed by imperfect wound healing and solar scar develop that photoage the skin.

The shelves in the cosmetics market are full of products treating extrinsic aging, but there is still a vacuum for a product, which targets intrinsic aging by inhibiting AGE in skin support proteins.

The ability to inhibit the formation of Advanced Glycation End products (in skin support proteins, like collagen) along with AGE breaker activity and Free Radical Scavenging activity, carries with it significant implications in treatment of Skin aging and wrinkles etc.

Thus, using the molecules, which can alter the presence of AGE, it is possible to prevent the signs of skin aging and wrinkle formation etc., and using them for cosmetic applications.

Experience shows that skin aging and wrinkle formation occur in-spite of good skin care. Hence, there is a need for development of an agent to prevent or treat aging of skin caused by formation of AGE. The compounds of the present invention are non-peptide, capable of modifying the AGE cross-link, formation in Collagen and Elastin. The compounds of the instant invention can be formulated along with other agents into a cosmetic preparation.

To prevent or delay skin wrinkles, it is important to inhibit formation of AGE, to reverse the already formed AGE as well as lower the oxidative stress by means of an antioxidant or free radical scavenger. Essentially a molecule that inhibits AGE; breaks AGE and slows down the formation of AGE and prevents collagen degradation, would be an ideal candidate for cosmeceuticals. The molecules of the instant invention exhibit the properties of being an AGE inhibitor and a potent AGE breaker well as free radical scavenger which make them most suitable for cosmetic applications.

Free radicals are atoms or molecules that have one or more unpaired electrons in their atomic structures and are highly reactive. Free radicals—reactive oxygen species (ROS)—are produced continuously in mammalian systems as a consequence of normal metabolic processes. Exogenous sources of ROS include exercise, pollution (especially cigarette smoke and car exhaust), alcohol, sunlight, and drugs (like anesthetics). Although free radicals have an important role in normal physiologic mechanisms, the excessive production of ROS results in oxidative stress—the terms usually applied to the out come of oxidative damage to biologically important molecules, such as protein, lipids, and nucleic acids. Proteins have long been known to be susceptible to oxidation by ROS. Aromatic amino acids like cystine, and disulfide bonds are particularly vulnerable. All biological materials contain a variety of polyunsaturated fatty acids, which are predominantly located in membrane lipids. They are highly susceptible to damage by ROS.

The group of compounds known as antioxidants (also referred to as "free radical scavengers") is the major defense against oxidative stress. These compounds function to protect membrane and cytosolic components against damage from ROS. Primary antioxidants, which prevent the formation of new radical species, include enzyme systems such as superoxide dismutase (SOD) and glutathione peroxidase (GSH Px). Secondary antioxidants trap radical species, thus preventing chain reactions, and include nutrients such as vitamin E, vitamin C, taurine and β-carotene. The final line of antioxidant defense is provided by the repair systems such as the enzyme methionine sulfoxide reductase that regenerates methionine residues within oxidized proteins and restores function.

Endogenous oxidative damage to cellular components, primarily proteins, lipids, and DNA is thought to contribute to the pathogenesis of numerous chronic diseases. The association between compromised antioxidant status, indices of oxidative damage, and clinical conditions like diabetes mellitus, asthma, chronic renal failure, hepatitis, colitis, atopic dermatitis, arthritis and various degenerative disorders is now well documented. There is considerable circumstantial evidence linking diminished antioxidant status including enzymes and nonezymatic scavengers, to increased oxidative damage and disease severity.

There is need of the molecules with ability to break/inhibit the protein cross linking, in addition of having anti-oxidant activity so that apart from their use in several disease conditions where oxidative stress plays vital role in the pathogenesis, they can be effectively used for cosmetic applications as mentioned below:

a) reversal and prevention of wrinkles,
b) reversal and prevention of fine lines,
c) promotion of epidermal growth,
d) photo protection of skin,
e) reversal and prevention of skin discoloration,
f) reversal and prevention of age spots,
g) conditioning and prevention of dry spot,
h) reversal and prevention of stretch marks,
i) reversal and prevention of blemishes,
j) skin care and conditioning,
k) reversal and prevention of senile xerosis,
l) conditioning and prevention of sun burns,
m) preventing and reversing the loss of collagen,
n) improving skin texture,
o) improving skin tone,
p) enhancing of skin thickness,
q) decreasing pore size,
r) restoring skin luster, s) minimising signs of fatigue,
t) reducing acne,
u) treatment of Telangiectasia and
v) improving aesthetic appearance of hair and nails.

Pharmaceutical Application of the Free-radical Scavenging (Anti-oxidant) Property of the Molecules.

Apart from the use of the compounds for cosmetic applications based on their AGE-breaking/AGE inhibiting and free-redical scavenging activities, the latter activity of these compounds can be used in strategies directed at control of oxidative stress for effective management of conditions discussed below:

Neuro-degenerative disorders such as Alzheimer's disease (A.D.), Parkinson's disease (P. D.), Huntington's disease (H.D.), Motor neuron disease (M.N.D), Prion disease As people age, their antioxidant levels diminish and these low levels are directly linked to the many diseases associated with aging such as Alzheimer's and Parkinson's disease. One of the leading hypotheses is that oxidative stress induced by Relative Oxygen Species (ROS) damages essential components of the neurons, resulting ultimately in the neuronal death. Oxidative stress is involved in various divergent events leading to neuronal damage, including an increase in membrane rigidity, DNA strand break, and impairment in glucose uptake. Several potential sources of oxidative stress in different neurodegenerative disorders have been well identified [Munch G, et al. 1998].

In A.D. mitochondrial dysfunction, amyloid beta mediated processes; transition metal accumulation and genetic factors are responsible for the redox imbalance [Smith M A, et al 2000].

Point mutations in Superoxide Dismutase enzymes are known in the familial form of MND.

Disturbances of neuronal energy metabolism have been implicated as a pathogenetic mechanism for H.D. [Browne S E, et al. 1999].

Diabetes and Diabetic Vascular Complications (DVCs)

The cause of oxidative stress in diabetes is not yet fully understood but is thought to be due to mitochondrial dysfunction, direct enzyme inhibition by hyperglycemia, auto-oxidation of glucose, and activation of nicotinamide-adenine dinucleotide phosphate (NADPH)-oxidase. Oxidative stress in diabetes is also increased due to weakened defenses due to reduced endogenous antioxidants. The oxidative stress manifests itself as elevated concentrations of lipid peroxidation products, erythrocyte fragility, and decreases in the antioxidant enzyme systems (CAT, GSH Px, SOD). Recent studies also have shown a positive correlation between blood glucose concentration and oxidant-induced lymphocyte DNA damage [E. J. Harper The $24^{th}$ Annual WALTHAM®/OSU SYMPOSIUM].

ROS are generated during glucose oxidation and formation of advanced glycosylation end products (AGE). Evidence has accumulated indicating that the generation of ROS plays an important role in the development of DVCs. Many biochemical pathways associated with hyperglycemia such as advanced glycosylation, glucose auto oxidation, and polyol pathway can increase the production of free radicals. Hyperglycemia in diabetic patients leads to excess auto-oxidation of glucose thereby reducing molecular oxygen and yielding oxidizing intermediates such as superoxide ions ($O_2^-$), hydroxyl radicals (.OH), and hydrogen peroxide ($H_2O_2$). Free radicals accelerate the formation of advanced glycosylation end products (AGE), because fragmentation and conformational changes occurring during glycosylation and glucose oxidation have been shown to be dependent upon free radicals. AGEs in turn supply more free radicals; this process is termed as oxidative glycosylation or glycoxidation. These free radicals impair vascular relaxation by inactivating or quenching nitric oxide (NO) and also adversely affect the endothelial function. Evidence also suggests that Maillard reaction acts as an amplifier of oxidative damage in aging and diabetes [D. Guigliano et al, 1996].

Intestinal Diseases

Oxidative stress is an important cause of tissue injury that occurs in inflammation and ischemia. Intestinal ischemia, radiation enteritis, inflammatory bowel disease, and promotion of gastric and colorectal cancers are some of the gastro-intestinal conditions where oxidative stress is implicated in the pathogenesis.

Liver Diseases

Alcoholic liver disease—Ethanol induces an increase in lipid peroxidation either by enhancing ROS or decreasing the level of endogenous antioxidants. Ethanol also induces variety of cytochrome P450 enzymes in microsomes and xanthine oxidases in cytosol. The role of these enzymes in the generation of oxidative stress has been well established in various studies [Ishii H, et al. 1997].

Chronic hepatitis C—Enhanced oxidative stress initiates a fibrogenesis cascade in the liver of patients with chronic hepatitis C. Evidences are coming up supporting an oxidative stress pathway leading to active fibrogenesis in chronic hepatitis C. This fibrogenesis cascade characteristic of severe chronic hepatitis C (e.g., oxidative stress, induction of c-myb, activation of stellate cells, and collagen gene expression) is stimulated by ROS.

Cancers

Oxidative damage to DNA is a result of interaction of DNA with ROS, in particular the hydroxyl radical. The hydroxyl radicals produce multiple modifications in DNA. Oxidative attack by OH radical on the deoxyribose moiety leads to the release of free bases from DNA, generating strand breaks with various sugar modifications and simple abasic (AP) sites.

ROS also interact with and modify cellular protein, lipid, and DNA, which results in altered target cell function. The accumulation of oxidative damage has been implicated in both acute and chronic cell injury including possible participation in the formation of cancer. Acute oxidative injury may produce selective cell death and a compensatory increase in cell proliferation. This stimulus may result in the formation of newly initiated preneoplastic cells and/or enhance the selective clonal expansion of latent initiated preneoplastic cells. Similarly, sublethal acute oxidative injury may produce unrepaired DNA damage and result in the formation of new mutations and, potentially, new initiated cells. ROS, therefore, can have multiple effects in the initiation stage of carcinogenesis by mediating carcinogen activation, causing DNA damage, and interfering with the repair of the DNA damage.

Benefits of various antioxidants in preventing or treating following cancers have been extensively studied.
1) Lung cancer
2) Colorectal cancer
3) Cervical cancer
4) Breast cancer
5) Malignant melanoma Oxidative Stress in Cardiac Diseases Lifelong high levels of antioxidant nutrients are supposed to protect against the development of heart disease. High doses of antioxidants in the month following an acute heart attack have been shown to significantly reduce the number of deaths, as well as the extent of cardiac damage in non-fatal cases.

It is currently thought that increase in oxidative stress is involved in the pathophysiology of endothelial dysfunction that accompanies a number of cardiovascular risk factors including hypercholesterolemia, hypertension and cigarette smoking. It also plays a pivotal role in the evolution of clinical conditions such as atherosclerosis and heart failure. Oxidative stress can activate redox-sensitive kinase cascades and transcription factors such as $NF_\kappa B$ and AP-1, with resulting increases in the expression of factors associated with an inflammatory response and cellular proliferation. There are three enzyme systems producing reactive oxygen species in the vascular wall: NADH/NADPH oxidase, xanthine oxidoreductase, and endothelial nitric oxide synthase (Zalba G. et. al, 2000, Rosenfeld M E, 1998).

Atherogenesis is regarded as the outcome of interactions among multiple stimuli. Endothelial dysfunction plays a key role in the development of atherosclerosis. Elevated homocysteine concentrations are associated with rapid onset of endothelial dysfunction, which is another mechanism by which increased oxidative stress contributes to atherosclerosis. Oxidation of low-density lipoprotein plays an important role at several steps in atherogenesis. Oxidative stress also activates $N_\kappa KB$, which induces expression of genes controlling cytokine expression and leukocyte adhesion to vascular wall. (Maxwell, et al. 1997).

Animal studies have provided evidence by suggesting that free radicals may promote thrombosis, directly damage vascular cells and other tissues, and interfere with vasomotor regulation with the clinical sequelae of myocardial infarction and ischemic stroke.

In tissues where oxygen supply becomes used up following ischemia, as in myocardial ischemia, the enzyme xanthine oxidase is changed to a form that has potential to reduce oxygen to superoxides. On readmission of oxygen e.g. by reperfusion there is a burst of free radical generation. ROS are formed at an accelerated rate in post-ischemic myocardium. Thus biochemical damage due to free radicals contributes to the ischemic injury.

Oxidative stress also seems to be one of the mechanisms that may produce membrane defects and result in intracellular calcium overload, and cardiac contractile dysfunction in the stunned myocardium.

Macular Degeneration and Cataract

Oxidative damage to lens of the eye with increase in age has a major contribution in cataract formation. Macular degeneration is also being recognized as a consequence of oxidative damage.

HIV Disease

Perturbation of anti-oxidant defense system has been observed in various tissues in HIV patients. Oxidative stress may contribute to several aspects of HIV disease pathogenesis such as viral replication, inflammatory response, and decreased immune cell proliferation, loss of immune function, apoptosis, chronic weight loss. Antioxidants may offer a promising treatment to HIV patients.

Chronic Obstructive Pulmonary Diseases (COPD)

Alteration in the alveolar and lung metabolism of glutathione is widely recognized as a central feature of many inflammatory lung diseases including COPD. These changes are a result of the alteration in the gene expression of the gamma-glutamyl cystine synthase (Gamma-GCS), the rate-limiting enzyme in glutathione synthesis. Oxidative stress is implicated in the pathogenesis of COPD, since it results in inactivation of anti proteinases, airspace epithelial injury, mucus hypersecretion, increased influx of neutrophils into the lungs, transcription factor activation and gene expression of pro-inflammatory mediators [MacNee W, et al. 2001].

Renal Disease

ROS have been implicated not only in the genesis of different forms of renal disease, predominantly experimentally induced glomerulonephritis, but also in different forms of acute renal failure.

Asthma

Although the pathogenesis of asthma is not fully defined, a typical feature is an increase in the number of inflammatory cells in the lung. Such cells generate ROS, which are involved in the pathophysiology of asthma, including airway smooth muscle contraction, increased airway reactivity, and increased vascular permeability.

Effect of Antioxidant Status on Immunologic Function

The immune system is particularly sensitive to oxidative stress, primarily because immune cells rely heavily on cell-to-cell communication to work effectively. Peroxidation of cell membranes compromises membrane integrity and disrupts intracellular signaling.

Cataract

Oxidative damage to lens of eye with increase in age has been a major contribution in cataract formation.
Thus, by scavenging the free radicals, the following diseases can be managed.
1) Neurodegenerative disorders
  (a) Alzheimer's Disease
  (b) Parkinson's Disease
  (c) Huntington's Disease
  (d) Motor Neuron Disease
  (e) Prion Disease
2) Diabetes and Diabetic Vascular Complications
3) Intestinal Diseases
  (a) Intestinal Ischemia
  (b) Radiation Enteritis
  (c) Inflammatory Bowel Disease
  (d) Gastric and Colorectal Cancers 4) Liver Diseases
   (a) Alcoholic Liver Disease
   (b) Chronic Hepatitis C
5) Cancers
   (a) Lung Cancer
   (b) Colorectal Cancer
   (c) Cervical Cancer
   (d) Breast Cancer
   (e) Malignant Melanoma
6) Cardiac Diseases
   (a) Atherosclerosis
   (b) Myocardial Infarction
   (c) Ischemic Stroke
   (d) Endothelial dysfunction
7) Opthalmic Disorders
   (a) Cataract formation
   (b) Macular degeneration
8) HIV Disease
9) Respiratory Diseases
   (a) Chronic Obstructive Pulmonary Diseases (COPD)
   (b) Asthma
10) Renal Diseases
    (a) Glomerulonephritis
    (b) Acute Renal failure

SUMMARY OF THE INVENTION

The first objective of the present invention is to provide a new class of five membered heterocyclic ring compounds which are useful for the management of diabetes and aging related vascular complications and particularly in the treatment of complications of diabetes mellitus and other aging related conditions such as vascular and neurovascular complications including kidney disease, nerve damage, atherosclerosis, retinopathy, inflammatory disorders, immunological disorders, oxidative stress and dermatological & cosmetic indications. The invention also extends the method to reverse the discoloration of teeth resulting from nonenzymatic browning in the oral cavity which comprises administration of an amount effective to reverse the pre-formed advanced glycosylation crosslinks.

The second object of the present invention is to provide compounds of five membered heterocyclic ring compounds, which exhibit AGE breaking and inhibiting activities.

The third object of the present invention is to provide a method of preparation of compounds of five membered heterocyclic ring compounds, which exhibit AGE breaking and inhibiting activities.

The fourth object of the invention is to provide pharmaceutical compositions with a new class of compounds of five membered heterocyclic ring compounds, according to the invention and their pharmaceutically acceptable salts in combination with suitable carriers, solvents, excepients, diluents and other media normally employed in preparing such compositions.

The fifth object of the invention is to provide a method of treatment of a diabetic patient by administration of the compounds of the invention, either singly or in combination with drugs for anti-diabetic therapy, or pharmaceutically acceptable salts thereof in required dosage in admixture with pharmaceutically acceptable diluent, solvent, excepients, carriers or other media as may be appropriate for the purpose.

The sixth object of the invention is to provide a new class of compounds having a) free radical scavenger activity b) AGE breaker activity and c) AGE inhibitor activity in the same molecule.

The seventh object of the invention is to provide a cosmetic composition comprising these compounds as active ingredients.

The eighth object of the invention is to provide a process for making the cosmetic composition.

The ninth object of the invention is to provide a method for cosmetic application by applying the cosmetic composition of the invention.

The tenth object of the invention is to provide a pharmaceutical composition useful for scavenging free-radicals from the body cells.

The eleventh object of the invention is to provide a method for scavenging free radicals from the body cells of a mammal.

The twelfth object of the invention is to provide a method of treatment of diseases caused by accumulation of free radicals in the body cells of a mammal.

The thirteenth object of the invention is to provide a method for inhibiting AGE and also a composition for inhibiting AGE in a mammal.

Another object of the invention is to provide a dialysis fluid useful for peritoneal dialysis of a diabetic patient.

The invention also provides for a method of cosmetic treatment by applying the composition as above. The invention further provides a pharmaceutical composition useful for scavenging free radicals from the body cells of a mammal comprising the compound as defined above or its pharmaceutically acceptable salts in admixture with a pharmaceutically acceptable carrier, diluent excipient or solvent.

The invention further provides a method of scavenging free radicals from the body cells of a mammal by administering the pharmaceutical composition as mentioned above or a method of treatment of diseases caused by accumulation of free radicals by administering the said composition.

The invention in addition provides a method for inhibiting AGE and a composition for inhibiting AGE by use of the compounds of invention.

DETAILED DESCRIPTION OF THE INVENTION

The present invention provides a new class of AGE-breakers of formula I

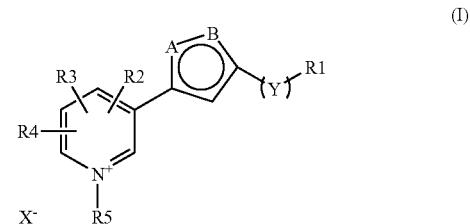

(I)

wherein

R1 is alkyl or aryl group;

Y is selected from the group consisting of sulfur, oxygen, nitrogen or alkyl;

A and B are independently selected from nitrogen, sulfur, oxygen or carbon to form heteroaromatic ring system;

R2, R3 and R4 are independently selected from the group consisting of F, Cl, Br, I, $OR_7$, $NO_2$, alkyl, aryl including heteroaryl, formyl, acyl, $C(O)NR_6R_7$, $C(O)OR_6$, $NR_6R_7$, N=C(R$_6$)(R$_7$), SR$_6$, SO$_2$NH$_2$, SO$_2$ alkyl, SO$_2$aryl; R$_2$, R$_3$ and R$_4$ might be optionally joined together to form a ring system;

If quaternized, R$_5$ is independently selected for the group consisting of alkyl or aryl; if not quaternized, R$_5$ is null, and X is null;

R$_6$ is independently selected from the group consisting of H, alkyl and aryl including heteroaryl provided R$_6$ might be different for R$_2$, R$_3$ and R$_4$ in the same compound;

R$_7$ is independently selected from the group consisting of H, alkyl and aryl including heteroaryl and in each case optionally different from substituent R$_6$, provided R$_7$ might be different for R$_2$, R$_3$ and R$_4$ in the same compound;

If quaternized, X is selected from group consisting of a halide ion, acetate ion, perchlorate ion, sulfonate ion, oxalate ion, citrate ion, tosylate ion, maleate ion, mesylate ion, carbonate ion, sulfite ion, phosphoric hydrogen ion, phosphonate ion, phosphate ion, BF$_4^-$ and PF$_6^-$ with proviso that when two alkyl groups are present on the same carbon or nitrogen, they are optionally linked together to form a cyclic structure.

As used herein, "alkyl" refers to an optionally substituted hydrocarbon group joined by single carbon-carbon bonds and having 1 to 8 carbon atoms joined together. The alkyl hydrocarbon group may be linear, branched or cyclic, saturated or unsaturated. The substituents are selected from F, Cl, Br, I, N, S, O and aryl. Preferably, no more than three substituents are present.

As used herein "aryl" refers to an optionally substituted aromatic group with at least one ring having a conjugated pi-electron system, containing up to two conjugated or fused ring systems. Aryl includes carbocyclic aryl, heterocyclic aryl and biaryl groups, all of which may be optionally substituted. The substituents are selected from F, Cl, Br, I, N, S, O and straight chain or branched C$_1$–C$_6$ hydrocarbon.

In a preferred embodiment the invention provides a new class of AGE breaker, AGE inhibitor and free radical scavengers of formula (1) and their pharmaceutically or cosmetically acceptable salts

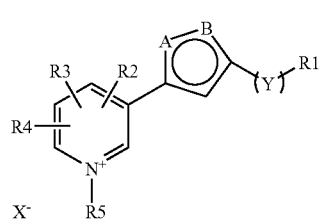

(I)

wherein,

R$_1$ is hydrogen or selected from linear or branched (C$_1$–C$_{12}$) alkyl, (C$_2$–C$_{12}$) alkenyl, (C$_3$–C$_7$) cycloalkyl, (C$_5$–C$_7$) cycloalkenyl, bicycloalkyl, bicycloalkenyl, heterocycloalkyl, aryl, aralkyl, heteroaryl, heteroaralkyl and wherein one or more heteroatoms when present are independently selected from O, N, or S and is optionally substituted, wherein the substituents are selected from a first group consisting of halogen, hydroxy, nitro, cyano, amino, oxo and oxime or from a second group consisting of linear or branched (C$_1$–C$_8$) alkyl, (C$_3$–C$_7$) cycloalkyl, alkylcycloalkyl, perhaloalkyl, perhalocycloalkyl, aryl, aralkyl, alkylaryl, alkylheteroaryl, aralkoxylalkyl, perhaloaryl, alkylheterocycloalkyl, heterocyclyloalkyl, perhaloheterocyclyloalkyl, heteroaryl, heteroaralkyl, alkylaryl, perhaloheteroaryl, acyl, alkoxyalkyl, thioalkyl and thioaryl, wherein the substitutents from said second group are optionally substituted by R$_{10}$ and are optionally and independently bridged by —(CO)O—, —(CO)NH—, —NH—, —NR$_8$—, —O—, —S—, —(SO)—, —(SO$_2$), —(SO$_2$)NH—, or —NH(CO)—;

Y is selected from the group consisting of null, (C$_1$–C$_{12}$) alkyl-Z or (C$_2$–C$_{12}$) alkyl, wherein Z is selected from sulfur, oxygen or nitrogen;

A and B are independently selected from NH, NR6, sulfur, oxygen or carbon to form a heteroaromatic ring system;

R$_2$, R$_3$ and R$_4$ are independently selected from a first group consisting of hydrogen, halogen, NO$_2$, N=C(R$_8$)(R$_9$), —NR$_8$R$_9$, —OR$_8$, perhaloalkyl, —(CO)NR$_8$R$_9$, —(CO)R$_8$, —(CO)OR$_8$, —O(CO)R$_8$, —NH(CO) R$_8$ or from a second group consisting of linear or branched (C1–C12) alkyl, (C2–C12)alkenyl, (C3–C7)cycloalkyl, (C5–C7)cycloalkenyl, bicycloalkyl, bicycloalkenyl, heterocycloalkyl, aryl, aralkyl, heteroaryl, heteroaralkyl, wherein one or more members of said second group when present are optionally substituted by R10 and wherein one or more heteroatoms when present are independently selected from O, N, or S;

R5 is null or selected from the group consisting of linear or branched (C$_1$–C$_{12}$)alkyl, (C$_2$–C$_{12}$)alkenyl, (C$_3$–C$_7$)cycloalkyl, (C$_{5-7}$)cycloalkenyl, bicycloalkyl; CH$_2$(CO)R$_7$, CH$_2$(CO)NHR$_8$, CH$_2$(CO)NR$_8$R$_9$, and CH$_2$(CO)OR$_7$ which are optionally substituted by R$_{10}$;

R$_6$ and R$_7$ are independently selected from the group consisting of linear or branched (C$_1$–C$_8$) alkyl, (C$_3$–C$_7$) cycloalkyl, alkylcycloalkyl, perhaloalkyl, perhalocycloalkyl, aryl, aralkyl, alkylaryl, alkylheteroaryl, aralkoxylalkyl, perhaloaryl, alkylheterocycloalkyl, heterocyclyloalkyl, perhaloheterocyclyloalkyl, heteroaryl, heteroaralkyl, alkylaryl, perhaloheteroaryl, acyl, benzoyl, alkoxyalkyl, thioalkyl and thioaryl wherein members of said group are optionally substituted by R10;

R$_8$ and R$_9$ are independently selected from the group consisting of linear or branched (C$_1$–C$_{12}$)alkyl, alkoxyaryl, alkoxyalkyl, alkoxycycloalkyl, alkoxyaryl, perhaloalkyl, (C$_2$–C$_{12}$)alkenyl, (C$_3$–C$_7$)cycloalkyl, perhalocycloalkyl, haloheterocycloalkyl, cyanoheterocycloalkyl, perhaloheterocycloalkyl, (C$_5$–C$_7$)cycloalkenyl, bicycloalkyl, bicycloalkenyl, heterocycloalkyl, aryl, aralkyl, heteroaryl, heteroaralkyl, perhaloaryl, perhaloheteroaryl wherein substituents of said group are optionally substituted by R$_{10}$;

R$_{10}$ is selected from halogen, hydroxy, nitro, cyano, amino, oxo, perhaloalkyl (C$_1$–C$_6$), or oxime;

X is selected from group comprising of a halide ion, acetate ion, perchlorate ion, sulfonate ion, oxalate ion, citrate ion, tosylate ion, maleate ion, mesylate ion, carbonate ion, sulfite ion, phosphoric hydrogen ion, phosphonate ion, phosphate ion, BF$_4^-$ and PF$_6^-$ provided when the groups/substituents are present on same or adjacent carbon or nitrogen atoms they together may optionally form a five or a six or a seven membered ring optionally containing one or more double bonds and optionally containing one or more heteroatoms selected from O, N, or S.

The compounds of formula (1) as defined above, is understood to include their analogs, their tautomeric forms, their stereoisomers, their polymorphs, their pharmaceutically acceptable solvates and their cosmetically acceptable solvates.

The non-limiting examples of pharmaceutically/cosmetically acceptable salts of the compounds of this invention include but not limited to salts of the carboxylic acid moiety such as alkali metal salts like Li, Na and K salts; alkaline earth metal salts like Ca and Mg salts; salts of organic bases for example lysine, arginine, guanidine, diethanolamine, choline, and the like; ammonium or substituted ammonium salts and aluminium salts; salts may be acid addition salts for example sulfates, nitrates, phosphates, perchlorates, borates, hydrohalides, acetates, tartrates, maleates, citrates, succinates, palmoates, methanesulfonates, benzoates, salicylates, hydroxynaphthoates, benzensulfonates, ascorbates, glycerophosphates, ketoglutarates and the like.

The following novel compounds are suggested by way of example alone of the representative compounds of the general formula I as defined above and in no way restrict the invention:

a) 1-(2-thien-2'-yl-2-oxoethyl)-3-[(3-phenyl methyl)pyrazol-5-yl]pyridinium bromide (compound 1);
b) 1-(2-thien-2'-yl-2-oxoethyl)-3-[(3-phenyl methyl)oxazol-5-yl pyridinium bromide (compound 2);
c) 1-(2-thien-2'-yl-2-oxoethyl)-3-[3-{1(2thien-2'-yl)-2oxoethyl pyridinium-4thio}methyl-pyrazol-5yl]pyridinium dibromide. (compound 3);
d) 1-(2-thien-2'-yl-2-oxoethyl)-3-[3-{1-(3,5-dimethylpyrazol-1-yl)methyl}pyrazol-5-yl]pyridinium bromide. (compound 4);
e) 1-(2-thien-2'-yl-2-oxoethyl)-3-[{3-phenylmethyl}-1-{2-pyridyl}-pyrazol-5-yl]-pyridinium bromide. (compound 5);
f) 1-(2-thien-2'-yl-2-oxoethyl)-3-[3{(3,5-dimethylpyrazol-1-yl)methyl-1-pyridyl}pyrazol-5-yl]pyridinium bromide. (compound 6);
g) 1-[2-(cyclopropylamino)-2-oxoethyl]3-[3-{(3,5-dimethyl pyrazol-1-yl)methyl}-pyrazol-5-yl]-pyridinium bromide. (compound 7);
h) 1-{2-(4-nitro-2-thienyl)-2-oxoethyl}-3-[3{(3,5-dimethylpyrazol-1-yl)methyl}-pyrazol-5-yl]-pyridinium bromide. (compound 8);
i) 1-(2-cyclopropylamino-2-oxoethyl)-3[(3-phenylmethyl)pyrazol-5-yl]pyridinium chloride. (compound 9);
j) 3,5-bis-[1-(2-thien-2'-yl-2-oxoethyl)-pyridinium-3-yl]-pyrazole dibromide. (compound 10);
k) 1-(2-thien-2'-yl-2-oxoethyl)-3-[(1-phenyl-3-phenylmethyl)pyrazol-5-yl]-pyridinium chloride. (compound 11);
l) 1-(2-(5'-methyl-2-thienyl)-2-oxoethyl)-3-[(3-phenylmethyl)pyrazol-5-yl]pyridinium chloride (compound 12);
m) 1-(2-thien-2'-yl-2-oxoethyl)3-[1-phenyl,3-{(3,5-dimethyl pyrazol-1-yl)methyl)}pyrazol-5-yl]-pyridinium chloride. (compound 13);
n) 1-(2-phenyl-2-oxoethyl)-3-[(3-phenylmethyl)pyrazol-5-yl]-pyridinium bromide. (compound 14);
o) 1-(2-cyclopropylamino-2-oxoethyl)3-[(1-phenyl-3-phenylmethyl)pyrazol-5-yl]-pyridinium chloride (compound 15);
p) 1-(2-(4-benzyl-1piperidinyl)-2-oxoethyl)3-[(3-phenoxymethyl)pyrazol-5-yl]-pyridinium bromide (compound 16);
q) 1-(2-phenyl-2-oxoethyl)-3-[(3-(3,5-dimethylpyrazol-1-yl)methyl)pyrazol-5-yl]-pyridinium chloride (compound 17);
r) 1-(2-(5-methyl-2-thienyl)-2-oxoethyl)-3-[(3-(3,5-dimethyl pyrazol-1-yl)methyl)pyrazol-5-yl]pyridinium chloride (compound 18);
s) 1-(2-phenyl-2-oxoethyl)-3-[(1-phenyl-3-phenylmethyl)pyrazol-5-yl]pyridinium chloride (compound 19);

t) 1-(2-(5-methyl-2-thienyl)-2-oxoethyl)-3-[(3(2-cyclohexyl ethyl)pyrazol-5-yl]pyridinium chloride (compound 20);
u) 1-(2-cyclopropylamino-2-oxoethyl)-3-[(3-(2-cyclohexyl-ethyl)pyrazol-5-yl]pyridinium chloride (compound 21);
v) 1-(2-phenyl-2-oxoethyl)-3-[(3-(2-cyclohexylethyl)pyrazol-5-yl]pyridinium chloride (compound 22);
w) 1-(2-cyclopropylamino-2-oxoethyl)-3-[(1-cyclohexyl-3-phenylmethyl)pyrazol-5-yl]pyridinium chloride (compound 23);
x) 1-(2-thien-2'-yl-2-oxoethyl)-3-[(3-phenoxymethyl)pyrazol-5-yl]pyridinium chloride (compound 24);
y) 1-[2-(1-adamantylamino)-2-oxoethyl]-3-[(3-phenylmethyl)pyrazol-5-yl]pyridinium chloride (compound 25);
z) 1-(2-phenyl-2-oxoethyl)-3-[{3-(3,5-dimethylpyrazol-1-yl)methyl)}1-phenyl-pyrazol-5-yl]pyridinium bromide (compound 26);
aa) 1-(2-(4-nitro-2-thienyl)-2-oxoethyl)-3-[(1-cyclohexyl-3-(3,5-dimethylpyrazol-1-yl)-methyl)pyrazol-5-yl]pyridinium bromide (compound 27);
bb) 1-(2-(4-nitro-2-thienyl)-2-oxoethyl)-3[(3-(2-cyclohexylethyl)pyrazol-5-yl]pyridinium bromide (compound 28);
cc) 1-(2-thien-2'-yl-2-oxoethyl)-3-[(1-phenyl-3-phenoxymethyl)pyrazol-5-yl]pyridinium chloride (compound 29);
dd) 1-(2-(4-nitro-2-thienyl)-2-oxoethyl)-3-[(1-phenyl-3-phenylmethyl)pyrazol-5-yl]pyridinium bromide (compound 30);
ee) pyrazole 1-(2-cyclopropylamino-2-oxoethyl)-3-[(3-phenoxymethyl)pyrazol-5-yl]pyridinium chloride (compound 31);
ff) 1-(2-cyclopropylamino-2-oxoethyl)-3-[(1-cyclohexyl-3-(3,5-dimethyl pyrazole)-1-yl) -5-yl]pyridinium chloride (compound 32);
gg) 1-(2-(5-chloro-2-thienyl)-2-oxoethyl)-3-[(3-phenoxymethyl)pyrazol-5-yl]pyridinium bromide (compound 33);
hh) 1-(2-phenyl-2-oxoethyl)-3-[(1-phenyl-3-phenoxymethyl)pyrazol-5-yl]pyridinium chloride (compound 34);
ii) 1-(2-thien-2'-yl-2-oxoethyl)-3-[(1-cyclohexyl-3-(3,5-dimethylpyrazol-1-yl-methyl)pyrazol-5-yl]pyridinium chloride (compound 35);
jj) 1-(2-cyclopropylamino-2-oxoethyl)-3-[(1-phenyl-3-phenoxymethyl)pyrazol-5-yl]pyridinium bromide (compound 36);
kk) 1-(2-thien-2'-yl-2-oxoethyl)-3-[(1-phenyl-3-(2-cyclohexylethyl)pyrazol-5-yl]pyridinium bromide (compound 37);
ll) 1-(2-thien-2'-yl-2-oxoethyl)-3-[(1-cyclohexyl-3-phenoxymethyl)pyrazol-5-yl]pyridinium chloride (compound 38);
mm) 3-[(3-phenylmethyl)pyrazol-5-yl]pyridine hydrochloride (compound 39);
nn) 3-[(3-phenoxymethyl)pyrazol-5-yl]pyridine hydrochloride (compound 40);
oo) 3-[(3,5-dimethylpyrazol-1-yl-methyl)pyrazol-5-yl]pyridine (compound 41);
pp) 3-[3-(2-cyclohexyl-ethyl)-pyrazol-5-yl]pyridine (compound 42);
qq) 1-(2-napthyl-2-oxo ethyl)-3[(3-phenoxymethyl)pyrazol-5-yl]pyridinium bromide (compound 43);
rr) 1-(phenylmethyl)-3[(3-phenyl methyl)pyrazol-5-yl]pyridinium chloride (compound 44);
ss) 1-(2-thien-2'-yl-2-oxo ethyl)-3[(3(-1-naphthyl)pyrazol-5-yl]pyridinium chloride (compound 45);
tt) 1-(2-phenyl-2oxoethyl)-3[3(thienyl-2-yl-methyl)pyrazol-5-yl]pyridinium chloride (compound 46);
uu) 1-(2-(5-methyl-2-thienyl)-2-oxoethyl)-3-[3(2-phenyl ethyl)pyrazol-5-yl]pyridinium chloride (compound 47);

vv) 1-(2-(5-methyl 2-thienyl)-2-oxo ethyl)-3-[3-(3-phenoxy propyl)pyrazol-5-yl]pyridinium chloride (compound 48);
ww) 1-(isopropyl)-3[(3-phenylmethyl)pyrazol-5-yl]pyridinium bromide (compound 49);
xx) 1-(2-(5-methyl-2-thienyl)-2-oxoethyl)-3-[(3-thiophenylmethyl)pyrazol-5-yl]pyridinium chloride (compound 50);
yy) 1-(2-thien-2'-yl-2-oxoethyl)-3[(3-(N-methyl-indole-3-yl methyl)pyrazol-5-yl]pyridinium chloride (compound 51);
zz) 1-(2-napthyl-2-oxo-ethyl)-3[(3-methyl)pyrazol-5-yl]pyridinium bromide (compound 52);
aaa) 1-(2-(1,4benzodioxane-6-yl-amino-2-oxoethyl)-3[(3-phenylmethyl)pyrazol-5-yl]pyridinium chloride (compound 53);
bbb) 1-(2-thien-2'-yl)-2-oxo ethyl)-3[(3-phenyl)pyrazol-5-yl]-5bromo-pyridinium chloride (compound 54);
ccc) 1-(2-(thien-2'-yl)-2-oxoethyl)-3[(3-phenyl)pyrazol-5-yl] quinolinium chloride (compound 55) and
ddd) 3-[(3-phenyl)pyrazol-5-yl)]quinoline (compound 56).

A compoundwise list of substituents of the above compounds in relation to the general structural formula (I) of the compounds as defined above is tabulated below:

TABLE 1

| Comp. No | R1 | R2 | R3 | R4 | R5 | A | B | Y | X |
|---|---|---|---|---|---|---|---|---|---|
| 1 | Phenyl | H | H | H | —CH$_2$—C(O)-2-thienyl | NH | N | —CH$_2$ | —Br |
| 2 | Phenyl | H | H | H | —CH$_2$—C(O)-2-thienyl | O | N | —CH$_2$ | —Br |
| 3 | Structure (a) | H | H | H | —CH$_2$—C(O)-2-thienyl | NH | N | —CH$_2$—S | —Br |
| 4 | Structure (b) | H | H | H | —CH$_2$—C(O)-2-thienyl | NH | N | —CH$_2$ | —Br |
| 5 | -Phenyl | H | H | H | —CH$_2$—C(O)-2-thienyl | N-(2-pyridyl) | N | —CH$_2$ | —Br |
| 6 | Structure (b) | H | H | H | —CH$_2$—C(O)-2-thienyl | N-(2-pyridyl) | N | —CH$_2$ | —Br |
| 7 | Structure (b) | H | H | H | —CH$_2$—C(O)—NH(Cyclopropyl) | NH | N | —CH$_2$ | —Cl |
| 8 | Structure (b) | H | H | H | —CH$_2$—C(O)-(5-nitro-2-thienyl) | NH | N | —CH$_2$ | —Br |
| 9 | Phenyl | H | H | H | —CH$_2$—C(O)—NH(Cyclopropyl) | NH | N | —CH$_2$ | —Cl |
| 10 | Structure (c) | H | H | H | —CH$_2$—C(O)-2-thienyl | NH | N | null | —Br |
| 11 | Phenyl | H | H | H | —CH$_2$—C(O)-2-thienyl | N-(phenyl) | N | —CH$_2$ | —Cl |
| 12 | Phenyl | H | H | H | —CH$_2$—C(O)-(5-methyl-thien-2-yl) | NH | N | —CH$_2$ | —Cl |
| 13 | Structure (b) | H | H | H | —CH$_2$—C(O)-2-thienyl | N-(phenyl) | N | —CH$_2$ | —Cl |
| 14 | Phenyl | H | H | H | —CH$_2$—C(O)-phenyl | NH | N | —CH$_2$ | —Br |
| 15 | Phenyl | H | H | H | —CH$_2$—C(O)—NH(Cyclopropyl) | N-(phenyl) | N | —CH$_2$ | —Cl |
| 16 | Phenyl | H | H | H | —CH$_2$—C(O)-(4-benzyl-piperidin-1-yl) | NH | N | —CH$_2$—O— | —Cl |
| 17 | Structure (b) | H | H | H | —CH$_2$—C(O)-phenyl | NH | N | —CH$_2$ | —Cl |
| 18 | Structure (b) | H | H | H | —CH$_2$—C(O)-(5-methyl-thien-2-yl) | NH | N | —CH$_2$ | —Cl |
| 19 | Phenyl | H | H | H | —CH$_2$—C(O)-phenyl | N-(phenyl) | N | —CH$_2$ | —Cl |
| 20 | Cyclohexyl | H | H | H | —CH$_2$—C(O)-(5-methyl-thien-2-yl) | NH | N | —CH$_2$—CH$_2$— | —Cl |
| 21 | Cyclohexyl | H | H | H | —CH$_2$—C(O)—NH(Cyclopropyl) | NH | N | —CH$_2$—CH$_2$— | —Cl |
| 22 | Cyclohexyl | H | H | H | —CH$_2$—C(O)-phenyl | NH | N | —CH$_2$—CH$_2$— | —Cl |
| 23 | Phenyl | H | H | H | —CH$_2$—C(O)—NH(Cyclopropyl) | N-(cyclohexyl) | N | —CH$_2$ | —Cl |
| 24 | Phenyl | H | H | H | —CH$_2$—C(O)-2-thienyl | NH | N | —CH$_2$—O— | —Cl |
| 25 | Phenyl | H | H | H | —CH$_2$—C(O)—NH-(1-adamantyl) | NH | N | —CH$_2$ | —Cl |
| 26 | Structure (b) | H | H | H | —CH$_2$—C(O)-phenyl | N-phenyl | N | —CH$_2$ | —Br |
| 27 | Structure (b) | H | H | H | —CH$_2$—C(O)-(4-nitro-thien-2-yl) | N-(cyclohexyl) | N | —CH$_2$ | —Br |
| 28 | Cyclohexyl | H | H | H | —CH$_2$—C(O)-(4-nitro-thien-2-yl) | NH | N | —CH$_2$—CH$_2$— | —Br |
| 29 | Phenyl | H | H | H | —CH$_2$—C(O)-2-thienyl | N-phenyl | N | —CH$_2$—O— | —Cl |
| 30 | Phenyl | H | H | H | —CH$_2$—C(O)-(4-nitro-thien-2-yl) | N-phenyl | N | —CH$_2$ | —Br |

TABLE 1-continued

| Comp. No | R1 | R2 | R3 | R4 | R5 | A | B | Y | X |
|---|---|---|---|---|---|---|---|---|---|
| 31 | Phenyl | H | H | H | —CH₂—C(O)—NH(Cyclopropyl) | NH | N | —CH₂—O— | —Cl |
| 32 | Structure (b) | H | H | H | —CH₂—C(O)—NH(Cyclopropyl) | N-(cyclohexyl) | N | —CH₂ | —Cl |
| 33 | Phenyl | H | H | H | —CH₂—C(O)-(5-chloro-thien-2-yl) | NH | N | —CH₂—O— | —Br |
| 34 | Phenyl | H | H | H | —CH₂—C(O)-phenyl | N-phenyl | N | —CH₂—O— | —Cl |
| 35 | Structure (b) | H | H | H | —CH₂—C(O)-2-thienyl | N-(cyclohexyl) | N | —CH₂ | —Cl |
| 36 | Phenyl | H | H | H | —CH₂—C(O)—NH(Cyclopropyl) | N-phenyl | N | —CH₂—O— | —Cl |
| 37 | Cyclohexyl | H | H | H | —CH₂—C(O)-2-thienyl | N-phenyl | N | —CH₂—CH₂— | —Cl |
| 38 | Phenyl | H | H | H | —CH₂—C(O)-2-thienyl | N-(cyclohexyl) | N | —CH₂—O— | —Cl |
| 39* | Phenyl | H | H | H | Null | NH | N | —CH₂ | Null |
| 40* | Phenyl | H | H | H | Null | NH | N | —CH₂—O— | Null |
| 41 | Structure (b) | H | H | H | Null | NH | N | —CH₂ | Null |
| 42 | Cyclohexyl | H | H | H | Null | NH | N | —CH₂—CH₂— | Null |
| 43 | Phenyl | H | H | H | —CH₂—C(O)-2-napthyl | NH | N | —CH₂—O— | —Br |
| 44 | Phenyl | H | H | H | —CH₂-phenyl | NH | N | —CH₂ | —Cl |
| 45 | 1-Napthyl | H | H | H | —CH₂—C(O)-2-thienyl | NH | N | —CH₂ | —Cl |
| 46 | 2-Thienyl | H | H | H | —CH₂—C(O)-2-phenyl | NH | N | —CH₂ | —Cl |
| 47 | Phenyl | H | H | H | —CH₂—C(O)-(5-methyl-thien-2-yl) | NH | N | —CH₂—CH₂— | —Cl |
| 48 | Phenyl | H | H | H | —CH₂—C(O)-(5-methyl-thien-2-yl) | NH | N | —CH₂—CH₂—CH₂—O— | —Cl |
| 49 | Phenyl | H | H | H | Isopropyl | NH | N | —CH₂ | —Br |
| 50 | Phenyl | H | H | H | —CH₂—C(O)-(5-methyl-thien-2-yl) | NH | N | —CH₂—S | —Cl |
| 51 | 1-methyl-indole-3-yl | H | H | H | —CH₂—C(O)-2-thienyl | NH | N | —CH₂ | —Cl |
| 52 | H | H | H | H | —CH₂—C(O)-2-napthyl | NH | N | —CH₂ | —Br |
| 53 | Phenyl | H | H | H | —CH₂—C(O)—NH-(3,4-ethylenedioxy-phenyl) | NH | N | —CH₂ | —Cl |
| 54 | Phenyl | H | 5-Br | H | —CH₂—C(O)-2-thienyl | NH | N | Null | —Cl |
| 55 | Phenyl | H | Benzene ring fused at 5,6 position | —CH₂—C(O)-2-thienyl | | NH | N | Null | —Cl |
| 56 | Phenyl | H | Benzene ring fused at 5,6 position | null | | NH | N | Null | —Cl |

*Isolated in the form of HCl salt.

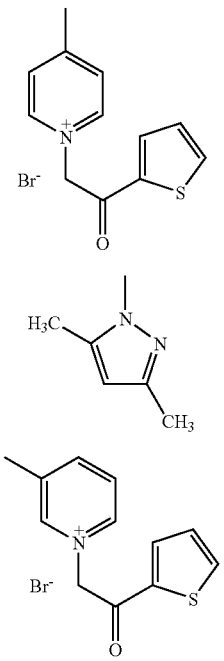

Structure (a)

Structure (b)

Structure (c)

According to the embodiment of the present invention, the present compounds are used for the treatment of diabetic complications, and aging related vascular and neurovascular complications including kidney disease, nerve damage, atherosclerosis, retinopathy, inflammatory disorders, immunological disorders, oxidative stress, dermatological & cosmetic indications and colouration of teeth occurring due to the higher levels of preformed AGE. The increased levels of preformed AGE can be brought under control by breaking/inhibiting the AGE products using compounds mentioned in the invention.

The novel compounds of the invention of general formula I can be synthesized. One way to prepare the compounds is by reacting α-substituted/unsubstituted acetyl pyridines with alkyl/aryl esters in the presence of a suitable base. Further, it is cyclized by various synthetic methods. If required, quarternization can be done with appropriate reagent by refluxing in alcoholic solvents like, methanol, ethanol, propanol, etc and high boiling solvents like toluene, xylene or DMF for 6–48 hrs. to give the desired compounds.

The examples of substituted pyridine derivatives which can be used for preparation of specific compounds of the invention are given below:
1. N,N'-bis(nicotinyl)hydrazine
2. 3-[(2-pyridyl)hydrazinocarbonyl]pyridine
3. 3-[2-methanesulfonyl)hydrazinocarbonyl]pyridine
4. 3-[(2-benzoyloxy)ethylaminocarbonyl]pyridine
5. 3-[(2-phenylsulfonyl)hydrazinocarbonyl]pyridine
6. 3-[(2-acetoxy)ethyloxycarbonyl]pyridine
7. 3-[(2-benzoyloxy)ethyloxycarbonyl]pyridine
8. 3-[(2-methoxy)ethyloxycarbonyl]pyridine
9. 3-[(2-phenylaminocarbonyl)hydrazinocarbonyl]pyridine
10. 3-[(2-acetoxy)ethylaminocarbonyl]pyridine
11. 3-[(2-(4-methylphenyl sulfonylhydrazinocarbonyl))]pyridine
12. 3-[(2-benzoyl)-hydrazino carbonyl]pyridine
13. 3-[(2-phenylmethane sulfonyl) hydrazino carbonyl]pyridine
14. 3-[(2-(3-cyclohexylpropanoyl)hydrazino carbonyl]pyridine
15. 3-[(2-methoxy)ethylaminocarbonyl]pyridine
16. 3-[1-oxo-1-(2-methoxycarbonyl)pyridyl]hydrazino pyridine The examples of quaternizing agents, which may be used in the reaction, are given below:
1. 2-bromoacetyl thiophene
2. 2-chloroacetyl thiopene
3. phenacylbromide
4. phenacylchloride
5. 2,4-dichloropheanacylbromide
6. N-phenyl chloroacetamide
7. N-cyclopropyl chloroacetamide
8. ethylbromoacetate
9. bromo acetylfuran
10. N-isopropylchloroacetamide
11. N-chloroacetyl-2-pyrrolidinone
12. chloroacetic acid In-vitro Screening for AGE-breaking Activity

EXAMPLE 1A

The in vitro AGE formation, studied in the laboratory, by incubating reducing sugar glucose, with protein bovine serum albumin, resulted in browning of solution and increase in the fluorescence. Fluorescence was used as the criteria to monitor the increased AGE formation.

Materials:
Bovine serum albumin (fraction V) (BSA)
Glucose, analytical grade
Phosphate buffered saline (PBS)

Equipment:
Microplate ELISA Reader-Spectramax Plus (Molecular Devices, USA)
Microplate washer, (Bio-Tec Instruments, USA)
pH meter
Methods of experiment: Elisa (Enzyme Linked Immunosorbent Assay)

160 mg/ml of protein, bovine serum albumin, BSA and 1.6M glucose sugar were dissolved in phosphate buffered saline, PBS. Sodium azide was added at 0.02% concentration as a preservative. The solution was filtered aseptically through a 0.22 μM filter and kept for aging at 37° C. for 16 weeks. After 16 weeks the solution was dialyzed against PBS, aliquoted and stored at −20° C.

To determine the AGE breaking activity, 10 μg/ml of the 16 weeks AGE-BSA was incubated with different concentrations of the test compounds at 37° C. for 24 hours and AGE breaking activity of the test compounds by ELISA was determined.

ELISA was Performed as Follows:
1. Different concentrations of 16 weeks AGE-BSA were coated on a microtiter plate as standard. Each concentration is coated in triplicates.
2. The test samples were coated on microtiter plate at a concentration of 5 ng. to 20 ng per well in triplicates.
3. The plate was incubated at 37° C. for one hour.
4. After incubation the plate was washed with PBST (PBS with 0.05% Tween 20).
5. Blocking with 5% skimmed milk in PBS at 37° C. for one hour was done.
6. The plate was washed with PBST.

7. Primary antibody against AGE-BSA was added and the plate is incubated at 37° C. for one hour.
8. The plate was washed with PBST.
9. Secondary antibody anti rabbit HRPO (Horse-Radish Per Oxidase) conjugate was added and the plate is incubated at 37° C. for one hour.
10. The plate was washed with PBST.
11. Colour development with OPD (orthophenylenediamine dihydrochloride) and hydrogen peroxide was done.
12. OD (optical density) at (450 nm reading −620 nm reading) was measured after incubation at 37° C. for 15 minutes with Microplate ELISA Reader.

The breaker activity of the compounds were determined by the following formula:

$$\% \text{ Breaker activity} = \frac{OD_{450-620}Control - OD_{450-620}Test}{OD_{450-620}Control} \times 100$$

$OD_{450-620}$Control=Absorbance of 20 ng AGE-BSA after incubation at 37° C. for 24 hours without test compound.

$OD_{450-620}$Test=Absorbance of 20 ng AGE-BSA after incubation at 37° C. for 24 hours with required concentration of test compound.

EXAMPLE 1B

Gel Permeation Chromatography Based Method

Gel Permeation Chromatography based method was used to determine AGE breaking activities of the compounds.

Principle:

Separation by Gel Permeation Chromatography (GPC) depends on differences in the size, more precisely the hydrodynamic volume, of the proteins in a sample. The larger molecules do not enter the pores of the column particles and elute in void volume of the column ($V_o$). The pores of a column particle are differentially accessible to smaller particles, depending on their size. This volume of the column is called ($V_1$). The total accessible volume ($V_t$) is the sum of the volume outside the particles ($V_o$) and the volume accessible inside the particles ($V_1$):

$$V_t = V_0 + V_i$$

Therefore, in a typical Gel Permeation Chromatography (GPC) run, high molecular weight molecules elute at a lower retention time whereas lower molecular weight molecules are retained for longer time. For the purpose of quantification, the area under the curve for the respective molecule is recorded. The same principle has been applied in the in vitro screening of the molecules of instant invention. Highly cross-linked Advanced Glycosylated Endproducts (AGE) were prepared in vitro by incubating Bovine Serum Albumin (BSA) with glucose for a period of 16 weeks. The molecular weight of BSA and AGE-BSA differs significantly on a GPC column and hence, there is a very good resolution between the two. The reduction in the area of AGE-BSA incubated in the presence of AGE breaker as compared to that of control AGE BSA (incubated in absence of AGE breaker) gives an estimate of the AGE breaker activity of the drug. In order to check the non-specific activity of the molecule, a similar experiment was repeated with BSA as well.

Methodology:

A known concentration of 16-week AGE-BSA was incubated with and without a predetermined concentration of the drug at 37° C. for 24 hours in clean transparent glass test tubes. The solution without drug served as the control and the solution containing the drug was treated as the test sample.

Gel permeation chromatography was performed on equal volumes of control AGE-BSA preparation and solution of AGE-BSA treated with drug. Average areas of the two chromatograms were calculated.

Two major peaks were observed in the chromatogram of the control and treated AGE-BSA samples:

Peak I=High molecular weight peak

Peak II=Low molecular weight peak

Peak I+Peak II=Total AGE-BSA

Calculations:

% Breakage in Peak I =
$$100 - \frac{\text{(Average area of Peak I in treated sample)}}{\text{(Average area of Peak I in control sample)}} \times 100$$

% Breakage in Peak II =
$$100 - \frac{\text{(Average area of Peak II in treated sample)}}{\text{(Average area of Peak II in control sample)}} \times 100$$

% Breakage Total =
$$100 - \frac{\text{(Average area of Peak I + Peak II in treated sample)}}{\text{(Average area of Peak I + Peak II in control sample)}} \times 100$$

Using representative compounds, the % AGE breaking activity was calculated and results recorded in Table 2 given below:

TABLE 2

| Sample (Compound No.) | Concentration (mM) | % Breakage |
|---|---|---|
| Compound 7 | 1.0 | 51.72 |
| Compound 8 | 5 | 85.31 |
| Compound 11 | 5.0 | 76.84 |
| Compound 12 | 10 | 89.23 |
| Compound 13 | 10 | 81.05 |
| Compound 14 | 10 | 58.14 |
| Compound 15 | 10 | 80.03 |
| Compound 16 | 10 | 95.51 |
| Compound 17 | 10 | 52.27 |
| Compound 18 | 5.0 | 52.97 |
| Compound 19 | 10 | 91.22 |
| Compound 21 | 10 | 93.43 |
| Compound 22 | 10 | 100.00 |
| Compound 23 | 10 | 53.29 |
| Compound 24 | 10 | 97.72 |
| Compound 25 | 5 | 98.59 |
| Compound 26 | 10 | 42.37 |
| Compound 27 | 10 | 86.98 |
| Compound 31 | 10 | 45.72 |
| Compound 34 | 10 | 100.0 |
| Compound 35 | 10 | 66.66 |
| Compound 37 | 10 | 85.45 |
| Compound 40 | 10 | 66.06 |

Thus, compounds 7, 8, 11–19, 21–25, 27, 34, 35, 37 and 40 exhibits very good AGE breaking activity, of which the potency of compounds 8, 11–13, 15, 16, 19, 21, 22, 24, 25, 27, 34 and 37 are significantly of high order.

AGE Inhibiting Activity of the Compounds

Further in view of the ability of the compounds of the instant invention to prevent the onset of AGE formation by the inhibitory action now discovered, development of pathology condition caused by AGE could be prevented or reduced. The dual activities of the compounds as AGE breaker and also as AGE inhibitor make them even more useful for the disease related to aging and diabetic complications, kidney diseases, nerve damage, retinopathy, neuropathy, endothelial dysfunction, atherosclerosis, micro angiopathy, browning that occurs in the oral cavity like browning of tooth, alzheimer, artirial compliance and distensibility, restenosis, abnormal tissue hindrance in peritoneal dialysis, erectile dysfunction and other dysfunction wherein the load of AGE on the cell is very crucial. In fact a triple action of the compounds (a) AGE breaker (b) AGE inhibitor (c) Free radical scavenger can be effectively utilized for reversal of prevention of several pathological conditions as well as reversal and prevention of cosmetic aspects of aging.

EXAMPLE 1C

Test for AGE Inhibiting Activity.

The following method was used to determine the inhibitory effect of the test compounds.

The following method was used to determine the inhibitory effect of the test compounds on Maillard reaction in-vitro. This method is adopted from U.S. Pat. No. 5,514,676 and European Patent No. 0 339 496 A2.

A solution of Bovine Serum Albumin (BSA), ribose and test compound was prepared in Phosphate Buffer Saline (PBS, pH 7.4) so as to have final concentration of BSA and ribose at 10 mg/ml and 500 mM respectively. Addition of compound was done in aseptic conditions. Sodium azide (0.02%) was also added in this solution in order to prevent microbial growth. A separate tube containing BSA, ribose and sodium azide in the same concentration and buffer as above, but without any test compound, was also incubated as positive control. After incubation at 37° C. for 7 days, 40 micro liter sample from each tube was removed and diluted with PBS to have final concentration of BSA at 1 mg/ml. The fluorescence of all the samples was measured at Excitation Maximum of 355 nM and the Emission Maximum of 460 nM using f-MAX Fluorimeter (Molecular Device, USA). In order to study the effect of test compound on fluorescence, freshly prepared compound solution was mixed with previously incubated positive control (i.e. BSA+ribose), so as to achieve same concentration of all the components as that of test samples.

The percent inhibition of test compound was measured as follows:

$$\% \text{ Inhibition} = \frac{F4 - F3}{F4} \times 100$$

Where F3=Fluorescence of BSA+ribose+compound,
F4 is fluorescence of incubated (BSA+ribose)+ freshly added test compound.

The representative compounds of general formula (I) have been tested for the activity as AGE inhibitor and the results recorded in Table 3 given below:

TABLE 3

| Compound No. | Concentration | % Inhibition (Day 7) |
|---|---|---|
| Compound 6 | 10 mM | 66 |
| Compound 10 | 2.5 mM | 75 |
| Compound 11 | 1.25 mM | 32.9 |
| Compound 13 | 10 mM | 57 |
| Compound 17 | 2.5 mM | 57.43 |
| Compound 18 | 5 mM | 79 |
| Compound 19 | 5 mM | 64.23 |
| Compound 22 | 2.5 mM | 51 |
| Compound 24 | 5 mM | 82.5 |
| Compound 26 | 5 mM | 61.45 |
| Compound 29 | 5 mM | 55.22 |
| Compound 34 | 5 mM | 60 |
| Compound 35 | 10 mM | 73.8 |

AGE Breakers:

As shown in Table 2, the compounds of the present invention are useful for breaking AGE. Hence, the compounds of the present invention can be used as a medicament in the treatment of diabetic complications and aging-related diseases, caused by accumulation of AGE. Also, these compounds can inhibit accumulation of AGE by breaking AGE, they can be used as a medicament for controlling and reducing the aggravation of disease conditions such as diabetes and aging related complications caused by accumulation of AGE.

The increased burden of AGE in any given tissue is likely to result into a pathological condition, and by different mechanisms thereafter may lead the various disease conditions. Thus, reducing the tissue burden of AGE the compounds of the instant invention can reverse these conditions, and the prevention of AGE accumulation up to a critical mass may prevent the condition from occurring in the first place. Indeed, in chronic diabetes and in old age there is a gradual accumulation of AGE over a period of years (Yong Ming Li et al., 1996; Brownlee, 1995). The complications associated with such mammals occur as the tissue burden of AGE increases over a period of time. The increase in tissue burden of AGE over time could be prevented in newly diagnosed patients by administering AGE breaker or inhibitor compounds sufficiently early. This method would prevent and/or delay the development of complications listed above in these patients.

AGE Inhibitors:

As shown in Table 3, the compounds of the present invention are also useful for inhibiting AGE.

Thus, can be used as a medicament in the treatment of diabetic complications and aging-related diseases caused by accumulation of AGE, as these compounds can inhibit the formation of AGE. Furthermore, the compounds can inhibit accumulation of AGE by inhibiting formation of AGE and they can be used as a medicament for preventing the diseases such as diabetes and aging related complications caused by accumulation of AGE.

Hence, the conditions listed bellow arising due to formation of AGE can be prevented or treated by the compounds of General formula (I) for two reasons: firstly due to their AGE breaking activity and secondly due to their AGE inhibiting activity. Infact, both the biological activities contribute to control the following desease conditions:

1. vascular and neuro-vascular complications,
2. nephrological disorder,
3. neurological disorder,
4. atherosclerosis, 5. retinal disorder,
6. dermatological disorder,
7. non-enzymatic browning of oral cavity,
8. endothelial or other organ dysfunction,
9. growth impairment,
10. inflammatory disorder,
11. immunological disorder,
12. oxidative stress,
13. aging and diabetic complication,
14. alzheimer disease,
15. restenosis, abnormal tissue hindrance in peritoneal dialysis,
16. abnormal tissue hindrance in peritoneal dialysis and
17. erectile dysfunction.

EXAMPLE 1D

Free Radical Scavenging Activity:

This method measures the relative ability of free radical scavenging substances to scavenge the ABTS.$^+$ i.e. 2,2-Azino-bis-(3-ethyl benzo thiazoline-6-sulfonate) radical cation as compared to a standard amount of standard or free radical scavengers antioxidants. Incubation of ABTS with Peroxidase (metmyoglobin) and hydrogen peroxide results in the production of radical cation ABTS.$^+$. This species is blue-green in colour and can be detected at 730 nm. Antioxidants or free radical scavengers in the added sample that causes suppression of the color to a degree that is proportional to their concentration.

Protocol:
Preparation of Buffer Solutions:
a. Phosphate Citrate Buffer (pH 5.0): 48.5 ml of 0.1M citric acid with sufficient 0.2M disodium hydrogen phosphate to produce 100 ml.
b. Phosphate Buffer Saline (PBS): Dissolve 40.0 g of NaCl, 1.0 g of KCl, 1.0 g of $KH_2PO_4$ and 3.05 g of $Na_2HPO_4$ in 1 liter milli-Q water. Dilute 200 ml of above solution to 1 liter with milli-Q water (pH 7.4–7.6).

Preparation of ABTS Stock Solution (2 mM):
1 tablet (10 mg) was dissolved in phosphate citrate buffer (pH 5.0) to give a 2 mM solution.

Preparation of Horse Radish Peroxidase Working Solution:
0.1 mg was dissolved in 10 ml of phosphate buffer saline, 1 ml of this solution was diluted to 100 ml with PBS.

Preparation of Hydrogen Peroxide (1.08 mM) Solution:
12 µl of Hydrogen Peroxide (30% w/v) was diluted to 100 ml with PBS.

Preparation of Drug Solutions:
0.1 mM of stock solution of the drug was prepared which was serially diluted in PBS to get 0.05 mM, 0.025 mM and 0.0125 mM solutions.

Preparation of ABTS Radical Stock Solution:
To 2 ml of ABTS stock solution, 1 ml of horseradish Peroxidase working solution was added.
As soon as 2 ml of Hydrogen peroxide solution was added to the above solution, blue-green colour of the ABTS radicals appeared. This solution was incubated at 30° C. for 30 min in order to ensure the completion reaction. Make up the volume to 10 ml with PBS.

Preparation of Control Solution:
900 µl of ABTS radical stock solution were added to an eppendorf tube. To it were added 100 µl of PBS solution.

Preparation of Test Solution:
900 µl of ABTS radical stock solutions were added to different eppendorf tubes. To it were added 100 µl of various concentrations of drug solution.

Measurement of Absorbance (O.D):
The absorbance of control and test samples was recorded immediately at 730 nm taking PBS as blank.

Calculation:
The percent antioxidant activity was calculated according to the formula:

% Antioxidant activity=100−[O.D of test sample/ O.D of control×100]

The results are tabulated in Table 4 below.

TABLE 4

| Compound No. | Relative Free Radical Scavenging Activity (%) on ABTS | | | |
|---|---|---|---|---|
|  | 12.5 µM | 25.0 µM | 50.0 µM | 100.0 µM |
| Compound 6 | 21.99 | 40.56 | 61.68 | 81.04 |
| Compound 8 | 22.22 | 38.18 | 67.14 | 99.71 |
| Compound 10 | 41.01 | 72.97 | 85.75 | 87.04 |
| Compound 11 | 26.78 | 45.74 | 70.61 | 86.46 |
| Compound 12 | 22.34 | 40.97 | 71.47 | 84.62 |
| Compound 13 | 23.58 | 41.78 | 64.01 | 82.54 |
| Compound 17 | 28.34 | 54.43 | 83.56 | 94.81 |
| Compound 18 | 28.65 | 53.8 | 84.41 | 95.32 |
| Compound 19 | 8.37 | 19.42 | 37.62 | 55.18 |
| Compound 20 | 6.15 | 9.06 | 34.31 | 57.75 |
| Compound 22 | 22.52 | 29.52 | 30.31 | 31.40 |
| Compound 24 | 43.66 | 74.64 | 83.24 | 90.12 |
| Compound 26 | 21.18 | 34.22 | 41.66 | 75.27 |
| Compound 27 | 16.16 | 27.12 | 39.05 | 51.04 |
| Compound 29 | 31.82 | 46.84 | 58.84 | 55.22 |
| Compound 34 | 13.2 | 19.08 | 26.39 | 29.40 |
| Compound 35 | 28.27 | 39.78 | 58.34 | 74.36 |
| Compound 37 | 21.79 | 37.92 | 41.95 | 39.46 |
| Compound 38 | 27.70 | 44.78 | 61.98 | 66.92 |

It is thus found that the compounds of general formula (I) as defined above are capable scavenging free radical, apart from inhibiting AGE and AGE breaker activities.

Discussion of the Test Results on Free Radical Scavenging Activity:

(i) For Cosmetic Application

Apart from the AGE breaking and free radical scavenging activity of the compounds of the invention their potential to inhibit AGE make them ideal for different cosmetic applications as discussed above.

The compounds of present invention have thus demonstrated capability of breaking AGE cross links formed in proteins. The compounds also demonstrated the capability of quenching free radicals, which can cause irreversible damage to proteins nucleic acids, etc. The ability to reverse the formation of Advanced Glycation End products (in skin support protein, like collagen and hair proteins like keratin) in conjunction with free radical quenching, carries with it significant implications and make them useful in cosmetic applications.

The compounds of present invention improves the aesthetic appearance of skin by arresting the complications of skin at more than one crucial stages. It breaks the preformed Advanced Glycation End products (AGE) formed in skin's support proteins and delays intrinsic aging (C. Jeanmaire et.al., British Journal of Dermatology 2001:145:10–18). The compounds of present invention also quenches the free radicals generated by UV exposure, pollutants etc, in the skin thereby prevents extrinsic or photoaging. The free radical quenching will also prevent the irreversible damage caused to proteins and nucleic acid. Moreover, by virtue of free radical quenching, these compounds will reduce the load of free radicals generated by Performed AGE's. The reduction in oxidative stress will in turn reduce the formation of reactive intermediates involved in Amadori Product formation.

The glycation of proteins is a universal phenomenon, well known at the skin level. However, this phenomenon can also occur in other related parts such as the nails or the hair, particularly in the Keratin (EP1068864 A1 and EP 1110539A1).

The glycation of the dermal proteins, particularly the collagen, leads to adverse cosmetic effects for e.g. consequences that damage the skin, the same consequences can be expected as a result of glycation of proteins in skin related parts, such as the nails and/or the hair, and in all the protein system.

The present invention discloses the molecules with ability to break the protein cross linking. In addition, these molecules have shown to have free radical scavenging (antioxidant) activity and thus useful in several disease conditions where oxidative stress plays vital role in the pathogenesis besides their cosmetic applications as discussed above.

Thus, the compounds of the instant invention are effective for atleast one of the following applications:
a) reversal and prevention of wrinkles,
b) reversal and prevention of fine lines,
c) promotion of epidermal growth,
d) photo protection of skin,
e) reversal and prevention of skin discoloration,
f) reversal and prevention of age spots,
g) conditioning and prevention of dry spot,
h) reversal and prevention of stretch marks,
i) reversal and prevention of blemishes,
j) skin care and conditioning,
k) reversal and prevention of senile xerosis,
l) conditioning and prevention of sun burns,
m) preventing and reversing the loss of collagen,
n) improving skin texture,
o) imporving skin tone,
p) enhancing of skin thickness,
q) decreasing pore size,
r) restoring skin luster,
s) minimising signs of fatigue,
t) reducing acne,
u) treatment of Telangiectasia and
v) improving aesthetic appearance of hair and nails.

i) For Non-Cosmetic Application

Apart from the use of the compounds of General Formula (I) for cosmetic applications based on their AGE-breaking/ AGE inhibiting and free-redical scavenging activities, the latter activity of these compounds can be used for control of oxidative stress for effective management of conditions.

The test compounds listed in the table above exhibit invitro free radical scavenging (antioxidant) activity. Excessive production of free radicals reactive oxidative species (ROS) results in oxidative stress. Therefore, these molecules would be very effective in reducing oxidative stress by their ability to trap ROS. Antioxidants (free radicals scavengers) are reported to be effective in the management of various diseases linked with oxidative stress selected from the group consisting of:

1) Neurodegenerative disorders
   (a) Alzheimer's Disease
   (b) Parkinson's Disease
   (c) Huntington's Disease
   (d) Motor Neuron Disease
   (e) Prion Disease
2) Diabetes and Diabetic Vascular Complications
3) Intestinal Diseases
   (a) Intestinal Ischemia
   (b) Radiation Enteritis
   (c) Inflammatory Bowel Disease
   (d) Gastric and Colorectal Cancers
4) Liver Diseases
   (a) Alcoholic Liver Disease
   (b) Chronic Hepatitis C
5) Cancers
   (a) Lung Cancer
   (b) Colorectal Cancer
   (c) Cervical Cancer
   (d) Breast Cancer
   (e) Malignant Melanoma
6) Cardiac Diseases
   (a) Atherosclerosis
   (b) Myocardial Infarction
   (c) Ischemic Stroke
   (d) Endothelial dysfunction
7) Opthalmic Disorders
   (a) Cataract formation
   (b) Macular degeneration
8) HIV Disease
9) Respiratory Diseases
   (a) Chronic Obstructive Pulmonary Diseases (COPD)
   (b) Asthma
10) Renal Diseases
    (a) Glomerulonephritis
    (b) Acute Renal failure Preparation of the Compounds of the Present Invention One possible non limiting method for preparing compounds of the present invention is given below:

The compounds of the present invention can be prepared according to the following steps Step—1: Formation of 1,3 diketo compound
Step—2: Cyclization Reaction
Step—3: Quaternization Reaction The following examples give method of preparation of the specific compounds according to the invention as listed in Table 1 above.

Step—1: Formation of 1,3 Diketo Compound

Method 1

1,3 Diketo compound can be prepared by reacting unsubstituted/substituted acetyl pyridines with alkyl/aryl esters in a suitable base.

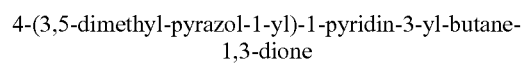

4-(3,5-dimethyl-pyrazol-1-yl)-1-pyridin-3-yl-butane-1,3-dione

To a suspension of potassium tertiary butoxide (16.5 gm. 0.147 mole) in dry THF i.e. Tetrahydro furan (150 ml) a mixture of 3-acetyl pyridine (18 gm., 0.148 mole) and ethyl-3,5-dimethyl pyrazolyl acetate diluted in THF (100 ml) was added at 5–10° C. under nitrogen atmosphere. Reaction mixture was then stirred at room temperature. (30° C.) for 6 hour. Then reaction mixture was poured into ice cold water with and $p_H$ was adjusted to ~4.0 with acetic acid and extracted with ethyl acetate (4×250 ml). Combined organic layer was washed with saturated saturated aqueous sodium chloride solution and finally organic layer was washed with water and dried over sodium sulphate. Ethyl acetate was concentrated u/v at 50° C. to yield crude product. Further tiluration with spatula in di ethyl ether yield a solid product. Separated solid was filtered and dried to yield required product.

Yield: 12.0 gm
$^1$H NMR (DMSO-d6 400 MHz) δ: 8.95 (1H, s), 8.75–8.73 (1H, d), 8.11–8.08 (1H, m), 7.42–7.39 (1H, m), 5.95 (1H, s), 5.78 (1H, s), 4.89 (2H, s), 2.28 (3H, s), 2.19 (3H, s).
MASS (m/z): 258, 259
IR (KBr cm$^{-1}$): 2924, 1621, 1557, 1455

Method 2

Alternatively, 1,3 Diketo compound can be prepared by reacting unsubstituted/substituted aryl esters with unsubstituted/substituted aryl methyl ketone in a suitable base.

Preparation of
1-Phenyl-3-quinoline-3-yl-propane-1,3-dione

A solution of ethyl-3-quinolinate (0.50 gm, 0.0025 mole) and acetophenone (0.30 gm, 0.0025 mole) was added to an ice-cold suspension of potassium tertiary butoxide in THF (5.0 ml). The reaction mixture was stirred at room temp. for 2 hours, acidified with a dilute acetic acid (10%). The resulting solid was filtered, air dried and recrystallised from boiling ethyl acetate to yield the desired product as a pale yellow colour solid.

Yield: 0.20 gm.
$^1$HNMR (DMSO-d$_6$ 400 MHz) δ: 9.58 (1H, s), 9.23 (1H, s), 8.25–8.13 (4H, m), 7.94 (1H, t), 7.77–7.62 (5H, m)
MASS (m/z): 272

Step—2: Cyclization Reaction

3-[3{(3,5-dimethyl pyrazol-1-yl methyl)-1-phenyl}pyrazol-5-yl]pyridine

To a stirred cold solution of 4-(3,5-dimethyl-pyrazol-1-yl)-1-pyridin-3-yl-butane-1,3-dione (0.8 gm., 0.003 mole) in methanol(30 ml) phenyl hydrazine(0.6 gm., 0.005 mole) in methanol (10 ml) was added slowly. Reaction mixture was stirred at room temperature (30° C.) For 3 hours and this was concentrated under reduce pressure to yield crude oily product. The crude product was purified over silica gel column using ethylacetate: hexane (1:1) as an eluent to afford the required product as yellow colour solid.

Yield: 0.6 gm.
$^1$H NMR (DMSO-d6, 400 MHz) δ: 8.52–8.50 (1H, d), 8.42 (1H, s), 7.59–7.56 (1H, m), 7.45–7.34 (4H, m), 7.28–7.26 (2H, m), 6.57 (1H, s), 5.83 (1H, s), 5.23 (2H, s), 2.31 (3H, s), 2.09 (3H, s).
MASS (m/z): 330, 331, 332

3-[3-(3,5-dimethyl-pyrazol-1-yl-methyl)pyrazole-5-yl]pyridine

To a stirred cold solution of 4-(3,5-dimethyl-pyrazol-1-yl)-1-pyridin-3-yl-butane-1,3-dione (2.5 gm., 0.0097 mole) in methanol (70 ml) Hydrazine hydrate (3.0 ml, 0.06 mole) was added slowly. Reaction mixture was stirred at room temperature (30° C.) for 3 hours and concentrated under reduced pressure to get an oily material. Chilled water was added and reaction mixture scratched with spatula yielded a solid. Seperated solid was filtered and recrystallised with methanol to yield a desire product.

Yield: 1.35 gm.
$^1$H NMR (DMSO-d6 400 MHz) δ: 8.98–8.95 (1H, d), 8.50–8.48 (1H, d), 8.11 (1H, s), 7.45–7.40 (1H, d), 6.66–6.61 (1H, d), 5.81 (1H, s), 5.21–5.14 (2H, d), 2.28 (3H, s), 2.07 (3H, s).
MASS (m/z): 254, 255

3-[3-{(3,5-dimethyl-pyrazol-1-yl methyl)-1-cyclohexyl}pyrazole-5-yl]pyridine

To a cold solution of trifluoroacetic acid (22.2 gm., 0.20 mole), 1-(t-butoxy carbonyl)cyclohexyl hydrazine (5.0 gm., 0.0236 mole) was added and stirred at room temperature (30° C.) for 30 minutes. Reaction mixture was concentrated under reduce pressure to yield a crude oily product. Water (10 ml) was added to crude product and neutralized with saturated solution of sodium bicarbonate. The neutralized solution was extracted with ethylacetate (3×75 ml). Combined organic layer was dried over sodium sulphate and concentrated under vacuum to yield a crude oily product (2.50 gm.)

Further oily product (2.50 gm., 0.022 mole) dissolved in methanol (10 ml) was added slowly to a solution of 4-(3,5-dimethyl-pyrazol-1-yl)-1-pyridin-3-yl-butane-1,3-dione(2.0 gm., 0.0078 mole) in methanol (20 ml). Reaction mixture was stirred at room temperature (30° C.) for 7 hours after that concentrated under reduced pressure to yield a brown colour oily product. Purification of crude product was done over silica gel column chromatography using 25% ethylacetate in hexane as eluent to afford the required product as white solid.

Yield: 0.96 gm.
$^1$H NMR (DMSO-d$_6$ 400 MHz) δ: 8.65–8.63 (1H, m), 7.85–7.82 (1H, m), 7.54–7.51 (1H, m), 6.15 (1H, s), 5.8 (1H, s), 5.13 (2H, s), 3.98 (1H, m), 2.27 (3H, s), 2.07 (3H, s), 1.91–1.85 (4H, m), 1.78–1.75 (2H, m), 1.62–1.559 (1H, m), 1.27–1.16 (3H, m)
MASS (m/z): 336, 337, 338

Synthesis of
3-[3-(phenylmethyl)-isoxazol-5-yl]-pyridine

A mixture of phenylnicotinoyl acetone 0.500 g (0.0021 mol), isopropyl alcohol (5 ml) and hydroxylamine free base (in 7 ml methanol) was stirred at room temperature for 3 days (72 hrs.). The reaction mixture was concentrated to dryness and purified by column chromatography using a mixture of ethylacetate and hexanes (3:1). The purified compound (oxime) was dissolved in IPA (10 ml) and to it was added 2 N HCl (4 drops). The reaction mixture was refluxed for 8 hrs. The reaction mixture is finally concentrated to dryness to yield the desired compound as a pale yellow solid:

Yield: 0.216 gm.
$^1$H NMR (CDCl$_3$, 400 MHz) δ: 9.01 (1H, s), 8.69 (1H, d), 8.20 (1H, d), 7.56 (m, 1H), 7.36–7.30 (m, 5H), 6.46 (1H, s), 4.11 (2H, s)
MASS (m/z): 237 (M$^+$+1)

Step—3: Quaternization Reaction

Quaternization of the substituted pyridine can be done with a quaternizing reagent in an alcoholic and/or high boiling solvent under reflux for 6–48 hrs. to give the desired compound if required.

EXAMPLE 2

1-(2-Thien-2'-yl-2-oxoethyl)-3-[3-{1-(3,5-dimethylpyrazol-1-yl) methyl}pyrazol-5-yl]pyridinium bromide (Compound 4)

To a suspension of 3-[3-(3,5-dimethyl-pyrazol-1-yl-methyl)pyrazole-5-yl]pyridine (0.5 gm., 0.002 mole) in IPA (35 ml) α-bromo 2-acetyl thiophene (0.46 gm., 0.0026 mole) was added. Reaction mixture was refluxed for 6 hours. Further cool to room temperature (30° C.). The solid separated was filtered and recrystallised using methanol and ethylacetate mixture to yield the required compound as a white solid.

Yield: 0.51 gm.

$^1$HNMR (DMSO-$d_6$, 400 MHz) δ: 13.66 (1H, s), 9.49 (1H, s), 9.03–9.01 (1H, d), 8.89–8.88 (1H, d), 8.26–8.21 (3H, m), 743–7.41 (1H, t), 6.77 (1H, s), 6.39 (2H, s), 5.84 (1H, s), 5.27 (2H, s), 2.27 (3H, s), 2.08 (3H, s),

MASS (m/z): 378, 379, 380

IR (KBr, cm$^{-1}$): 1676, 1638, 1591

The compounds of the invention as identified by their physio chemical data given in example 3–57 below have been prepared by following the above synthetic method.

EXAMPLE 3

1-(2-Thien-2'-yl-2-oxoethyl)-3-[(3-phenyl methyl) pyrazol-5-yl]pyridinium bromide (Compound 1)

Yield: 51%

IR (KBr, cm$^{-1}$): 1656, 1637, 1572

$^1$H NMR (DMSO-$d_6$, 400 MHz)δ: 13.44 (1H, s), 9.46 (1H, s), 8.98 (1H, d), 8.86 (1H, d), 8.24 (3H, m), 7.41 (1H, t), 7.34–7.30 (5H, m), 6.69 (1H, s), 6.38 (2H, s), 4.06 (2H, s)

MASS (m/z): 360, 361, 362, 363

EXAMPLE 4

1-(2-Thien-2'-yl-2-oxoethyl)-3-[(5-phenyl methyl) oxazol-3-yl pyridinium bromide (Compound 2)

Yield: 36%

IR (KBr, cm): 1747, 1671, 1456

$^1$HNMR (DMSO-$d_6$, 400 MHz) δ: 9.65 (1H, s), 9.12–9.08 (2H, m) 8.39 (1H, t) 8.26–8.23 (2H, m), 7.42 (1H, m) 7.38 0 7.33 (5H, m), 7.23 (1H, s) 6.40 (2H, s), 4.15 (2H, s)

MASS (m/z): 361, 362, 363

EXAMPLE 5

1-(2-thien-2'-yl-2-oxoethyl)-3-[3-{1-(2-thien-2'-yl)-2-oxoethyl pyridinium-4-thio}methyl-pyrazol-5-yl] pyridinium dibromide (Compound 3)

Yield: 71%

IR (KBr, cm$^{-1}$) 1666, 1500, 1451

$^1$H NMR (DMSO-$d_6$, 400 MHz) δ: 13.81 (1H, s), 9.54 (1H, s), 9.03–9.01 (1H, d), 8.93–8.91 (1H, d), 8.71–8.69 (2H, d), 8.30–8.13 (7H, m), 7.44–7.39 (2H, m), 7.09 (1H, s), 6.42 (2H, s), 6.21 (2H, s), 4.84 (2H, s)

MASS (m/z): 517, 518, 519, 520

EXAMPLE 6

1-(2-Thien-2'-yl-2-oxoethyl)-3-[{3-phenylmethyl}-1-{2-pyridyl}-pyrazol-5-yl]-pyridinium bromide (Compound 5)

Yield: 22%

IR (KBr, cm$^{-1}$): 1671, 1585, 1550

$^1$H NMR (DMSO-$d_6$, 400 MHz) δ: 9.24 (1H, s), 8.96–8.95 (1H, d), 8.24–8.21 (2H, m), 8.19–8.18 (1H, d), 8.15–8.14 (1H, d), 8.07–8.02 (1H, m), 7.97–7.95 (1H, d), 7.41–7.31 (6H, m), 7.25–7.22 (1H, m), 6.76 (1H, s), 6.32 (2H, s), 4.08 (2H, s)

MASS (m/z): 437, 438, 440

EXAMPLE 7

1-(2-Thien-2'-yl-2-oxoethyl)-3-[3{(3,5-dimethylpyrazol-1-yl)methyl-1-(2-pyridyl)}pyrazol-5-yl] pyridinium bromide (Compound 6)

Yield: 31%

IR (KBr, cm$^{-1}$): 3418, 3069, 2929, 1670, 1507, 1470

$^1$H NMR (DMSO-$d_6$, 400 MHz) δ: 9.25 (1H, s), 8.97–8.95 (1H, d), 8.61–8.59 (1H, d), 8.24–8.16 (4H, m), 8.09–8.05 (1H, m), 7.94–7.92 (1H, d), 7.42–7.39 (2H, m), 6.72 (1H, s), 6.33 (2H, s), 5.85 (1H, s), 5.31 (2H, s), 2.33 (3H, s), 2.08 (3H, s)

MASS (m/z): 455, 456, 457, 458

EXAMPLE 8

1-[2-(Cyclopropylamino)-2-oxoethyl]3-[3-{(3,5-dimethyl pyrazol-1-yl)methyl}-pyrazol-5-yl]-pyridinium bromide (Compound 7)

Yield: 59%

IR (KBr, cm$^{-1}$): 3373, 3064, 1667, 1577

$^1$H NMR (DMSO-$d_6$, 400 MHz) δ: 13.69 (1H, s), 9.41 (1H, s), 8.95 (1H, d), 8.55 (1H, d), 8.54 (1H, d), 8.16 (1H, t), 6.80 (1H, s), 5.84 (1H, s), 5.39 (2H, s), 5.26 (2H, s), 3.89–3.82 (1H, m), 2.27 (3H, s), 2.08 (3H, s), 1.12 (4H, d)

MASS (m/z): 353, 354, 355

EXAMPLE 9

1-{2-(4-Nitro-2-thienyl)-2-oxoethyl}-3-[3{(3,5-dimethylpyrazol-1-yl)methyl}-pyrazol-5-yl]-pyridinium bromide (Compound 8)

Yield: 24%

IR (KBr, cm$^{-1}$):

$^1$H NMR (DMSO-$d_6$, 400 MHz) δ: 13.70 (1H, s), 9.47 (1H, s), 9.30 (1H, s), 9.03 (1H, d), 8.87–8.85 (2H, m), 8.26

(1H, t), 6.77 (1H, s), 6.42 (2H, s), 5.84 (1H, s), 5.27 (2H, s), 2.27 (3H, s), 2.07 (3H, s),

MASS (m/z): 423, 424

EXAMPLE 10

1-(2-Cyclopropylamino-2-oxoethyl)-3-[(3-phenylmethyl)pyrazol-5-yl]pyridinium chloride (Compound 9)

Yield: 36%

IR (KBr, cm$^{-1}$): 3653, 3436, 3061, 1674, 1567, 1479

$^1$H NMR (DMSO-d$_6$, 400 MHz) δ: 13.46 (1H, s), 9.37 (1H, s), 8.93 (1H, d), 8.82 (1H, d), 8.72–8.71 (1H, d), 8.19–8.14 (1H, t), 7.36–7.23 (5H, m), 6.72 (1H, s), 5.38 (2H, s), 4.06 (2H, s), 2.71–2.66 (1H, m), 0.70–0.66 (2H, m), 0.50–0.46 (2H, m)

MASS (m/z): 333, 334, 335

EXAMPLE 11

3,5-Bis-[1-(2-thien-2'-yl-2-oxoethyl)-pyridinium-3-yl]-pyrazole dibromide (Compound 10)

Yield: 34%

IR (KBr, cm$^{-1}$): 3425, 3088, 2927, 1673, 1505, 1407.

$^1$H NMR (DMSO-d$_6$, 400 MHz)δ: 9.66 (2H, s), 9.09–9.02 (4H, m), 8.41 (2H, bs), 8.27–8.26 (4H, m), 7.66 (1H, s), 7.45–7.43 (2H, t), 6.47 (4H, s)

MASS (m/z): 471, 472, 473, 474

EXAMPLE 12

1-(2-Thien-2'-yl-2-oxoethyl)-3-[(1-phenyl-3-phenylmethyl)pyrazol-5-yl]-pyridinium chloride (Compound 11)

Yield: 42%

IR (KBr, cm$^{-1}$): 3302, 3029, 1672, 1503.

$^1$H NMR (DMSO-d$_6$, 400 MHz) δ: 9.20 (1H, s), 8.94–8.93 (1H, d), 8.24–8.20 (3H, m), 8.16–8.13 (1H, m), 7.50–7.31 (10H, m), 7.25–7.23 (1H, m), 6.73 (1H, s), 6.32 (2H, s), 4.06 (2H, s)

MASS (m/z): 436, 437, 438, 439, 440

EXAMPLE 13

1-(2-(5-Methyl-2-Thienyl)-2-oxoethyl)-3-[(3-phenylmethyl)pyrazol-5-yl]pyridinium chloride (Compound 12)

Yield: 44%

IR (KBr, cm$^{-1}$): 3745, 1654, 1518, 1455.

$^1$H NMR (DMSO-d$_6$, 400 MHz) δ: 13.52 (1H, s), 9.48 (1H, s), 8.99–8.97 (1H, d), 8.90–8.88 (1H, d), 8.24–8.21 (1H, t), 8.04–8.03 (1H, d), 7.35–7.22 (5H, m), 7.14–7.13 (1H, d), 6.70 (1H, s), 6.36 (2H, s), 4.07 (2H, s), 2.59 (3H, s)

MASS (m/z): 374, 375, 376, 377

EXAMPLE 14

1-(2-Thien-2'-yl-2-oxoethyl)-3-[1-phenyl, 3-{(3,5-dimethylpyrazol-1-yl)methyl)}pyrazol-5-yl]-pyridinium chloride (Compound 13)

Yield: 27%

IR (KBr, cm$^{-1}$):

$^1$H NMR (DMSO-d$_6$, 400 MHz) δ: 9.22 (1H, s), 8.95–8.93 (1H, d), 8.25–8.21 (3H, m), 8.16–8.12 (1H, m), 7.64–7.60 (1H, m), 7.50–7.46 (2H, m), 7.42–7.36 (3H, m), 6.71 (1H, s), 6.33 (2H, s), 5.84(1H, s), 5.28 (2H, s), 2.29 (3H, s), 2.08 (3H, s)

MASS (m/z): 454, 455, 456, 457, 458.

EXAMPLE 15

1-(2-Phenyl-2-oxoethyl)-3-[(3-phenylmethyl)pyrazol-5-yl]-pyridinium bromide (Compound 14)

Yield: 14%

IR (KBr, cm$^{-1}$): 3746, 3099, 1691, 1518.

$^1$H NMR (DMSO-d$_6$, 400 MHz) δ: 13.44 (1H, s), 9.45 (1H, s), 9.01–8.99 (1H, d), 8.85–8.84 (1H, d), 8.26–8.23 (1H, t), 8.07–8.06 (2H, d), 7.82–7.78 (1H, t), 7.69–7.65 (2H, t), 7.36–7.21 (5H, m), 6.68 (1H, s), 6.45 (2H, s), 4.07 (2H, s)

MASS (m/z): 354, 355

EXAMPLE 16

1-(2-Cyclopropylamino-2-oxoethyl) 3-[(1-phenyl-3-phenylmethyl)pyrazol-5-yl]-pyridinium chloride (Compound 15)

Yield: 7%

IR (KBr, cm$^{-1}$): 3395, 3026, 1689, 1503.

$^1$H NMR (DMSO-d$_6$, 400 MHz) δ: 9.15 (1H, s), 8.86 (1H, s), 8.71 (1H, s), 8.14–8.05 (2H, m), 7.44–7.23(10H, m), 6.74 (1H, s), 5.31 (2H, s), 4.05 (2H, s), 2.66 (1H, s), 0.68–0.67 (2H, s), 0.46 (2H, s).

MASS (m/z): 409, 410, 411, 412

EXAMPLE 17

1-(2-(4-Benzyl-1-piperidinyl)-2-oxoethyl) 3-[(3-phenoxymethyl)pyrazol-5-yl]-pyridinium bromide (Compound 16)

Yield:

IR (KBr, cm$^{-1}$): 3060, 1656, 1594

$^1$H NMR (DMSO-d$_6$, 400 MHz) δ: 13.84 (1H, s), 9.45 (1H, s), 8.98 (1H, d), 8.83 (1H, d), 8.21 (1H, t), 7.35–7.27 (4H, m), 7.23–7.19 (3H, m), 7.09–7.04 (3H, m), 6.98 (1H, t), 5.83–5.73 (2H, m), 5.21 (2H, s), 4.29 (1H, d), 3.75 (1H, d), 3.17–3.0 (1H, m), 2.69–2.63 (1H, m), 2.56 (2H, d), 1.99–1.84 (1H, m), 1.72–1.60 (2H, m), 1.36–1.28 (1H, m), 1.10–1.04 (1H, m)

MASS (m/z): 467, 468, 469

EXAMPLE 18

1-(2-Phenyl-2-oxoethyl)-3-[(3-(3,5-dimethylpyrazol-1-yl)methyl)pyrazol-5-yl]-pyridinium chloride (Compound 17)

Yield: 24%

IR (KBr, cm$^{-1}$): 3049, 2994, 1692, 1552.

$^1$H NMR (DMSO-d$_6$, 400 MHz) δ: 13.76 (1H, s), 9.50 (1H, s), 9.03–9.02 (1H, d), 8.90–8.88 (1H, d), 8.26 (1H, bs), 8.08–8.06 (2H, d), 7.81–7.78 (1H, m), 7.68–7.65 (2H, m), 6.75 (1H, s), 6.49 (2H, s), 5.83 (1H, s), 5.26 (2H, s), 2.26 (3H, s), 2.06 (3H, s).

MASS (m/z): 372, 373, 374.

EXAMPLE 19

1-(2-(5-Methyl-2-thienyl)-2-oxoethyl)-3-[(3,-(3,5-dimethyl pyrazol-1-yl)methyl)pyrazol-5-yl]pyridinium chloride (Compound 18)

Yield: 34%

IR (KBr, cm$^{-1}$): 3322, 2923, 1659, 1552.

$^1$HNMR (DMSO-d$_6$, 400 MHz) δ: 13.71 (1H, s), 9.48 (1H, s), 9.01–8.99 (1H, d), 8.89–8.87 (1H, d), 8.23 (1H, bs), 8.04–8.03 (1H, d), 7.13 (1H, s), 6.76 (1H, s), 6.33 (2H, s), 5.83 (1H, s), 5.26 (2H, s), 2.58 (3H, s), 2.26 (3H, s), 2.07 (3H, s)

MASS (m/z): 392, 393, 394, 395

EXAMPLE 20

1-(2-Phenyl-2-oxoethyl)-3-[(1-phenyl-3-phenylmethyl)pyrazol-5-yl]pyridinium chloride (Compound 19)

Yield: 63%

IR (KBr, cm$^{-1}$): 3351, 3235, 3030, 1694, 1504.

$^1$H NMR (DMSO-d$_6$, 400 MHz) δ: 9.17 (1H, s), 8.93–8.91 (1H, d), 8.25–8.23 (1H, d), 8.17–8.14 (1H, t), 8.06–8.04 (2H, d), 7.81–7.78 (1H, t), 7.68–7.64 (2H, t), 7.49–7.44 (3H, m), 7.38–7.30 (6H, m), 7.24–7.20 (1H, m), 6.72 (1H, s), 6.40 (2H, s), 4.05 (2H, s).

MASS (m/z): 430, 431, 432

EXAMPLE 21

1-(2-(5-Methyl-2-thienyl)-2-oxoethyl)-3-[(3 2-cyclohexyl ethyl)pyrazol-5-yl]pyridinium chloride (Compound 20)

Yield: 30%

IR (KBr, cm$^{-1}$): 3072, 2920, 1658, 1519, 1450.

$^1$H NMR (DMSO-d$_6$, 400 MHz) δ: 13.33 (1H, s), 9.52 (1H, s), 8.99–8.97 (1H, d), 8.92–8.90 (1H, d), 8.26–8.22 (1H, t), 8.06–8.05 (1H, d), 7.14 (1H, s), 6.76 (1H, s), 6.40 (2H, s), 2.71–2.67 (2H, t), 2.59 (3H, s), 1.75–1.63 (5H, m), 1.57–1.52 (2H, q), 1.24–1.16 (4H, m), 0.95–0.90 (2H, m).

MASS (m/z): 394, 395, 396

EXAMPLE 22

1-(2-Cyclopropylamino-2-oxoethyl)-3-[(3-(2-cyclohexylethyl)pyrazol-5-yl]pyridinium chloride (Compound 21)

Yield: 39%

IR (KBr, cm$^{-1}$): 3174, 2923, 1682, 1548.

$^1$H NMR (DMSO-d$_6$, 400 MHz) δ: 13.25 (1H, s), 9.40 (1H, s), 8.94–8.91 (1H, d), 8.85–8.84 (1H, d), 8.60–8.58 (1H, d), 8.18–8.15 (1H, m), 6.79 (1H, s), 5.43 (2H, s), 3.90–3.85 (1H, m), 2.71–2.67 (2H, t), 1.75–1.63 (5H, m), 1.58–1.52 (2H, q), 1.24–1.12 (8H, m), 0.96–0.88 (2H, m)

MASS (m/z): 355, 356, 357.

EXAMPLE 23

1-(2-Phenyl-2-oxoethyl)-3-[(3-(2-cyclohexylethyl)pyrazol-5-yl]pyridinium chloride (Compound 22)

Yield: 65%

IR (KBr, cm$^{-1}$): 3059, 2924, 1698, 1519. $^1$H NMR (DMSO-d$_6$, 400 MHz) δ: 13.26 (1H, s), 9.49 (1H, s), 9.00–8.98 (1H, d), 8.88–8.86 (1H, d), 8.28–8.24 (1H, m), 8.09–8.07 (2H, d), 7.83–7.79 (1H, t), 7.70–7.66 (2H, t), 6.75 (1H, s), 6.50(2H, s), 1.75–1.61 (5H, m), 1.58–1.52 (2H, q), 1.27–1.08 (4H, m), 0.96–0.88 (2H, m).

MASS (m/z): 374, 375, 376

EXAMPLE 24

1-(2-Cyclopropylamino-2-oxoethyl)-3-[(1-cyclohexyl-3-phenylmethyl)pyrazol-5-yl]pyridinium chloride (Compound 23)

Yield: 9%

IR (KBr, cm$^{-1}$): 3165, 2994, 1662, 1500, 1452.

$^1$H NMR (DMSO-d$_6$, 400 MHz) δ: 9.11 (1H, s), 9.01–9.00 (1H, d), 8.69–8.67 (1H, d), 8.60–8.58 (1H, d), 8.27–8.24 (1H, m), 7.33–7.29 (4H, m), 7.22–7.19 (1H, m), 6.38 (1H, s), 5.42 (2H, s), 4.08–4.02 (1H, m), 3.96 (2H, s), 3.91–3.85 (1H, m), 1.89 (4H, bs), 1.78–1.75 (2H, d), 1.64–1.61 (1H, d), 1.41 (2H, bs), 1.21–1.16 (1H, m), 1.13–1.12 (4H, d)

MASS (m/z): 417, 418, 419

EXAMPLE 25

1-(2-Thien-2'-yl-2-oxoethyl)-3-[(3-phenoxymethyl)pyrazol-5-yl]pyridinium chloride (Compound 24)

Yield: 18%

IR (KBr, cm$^{-1}$): 3060, 2957, 1665, 1595, 1491.

$^1$H NMR (DMSO-d$_6$, 400 MHz) δ: 13.82 (1H, s), 9.55 (1H, s), 9.06–9.04 (1H, d), 8.93–8.91 (1H, d), 8.30–8.22 (3H, m), 7.44–7.43 (1H, m), 7.35–7.31 (2H, m), 7.08–7.05 (3H, m), 7.01–6.97 (1H, m), 6.43 (2H, s), 5.22 (2H, s)

MASS (m/z): 376, 377, 378

EXAMPLE 26

1-{2-(1-Adamantylamino-2-oxoethyl)}-3-[(3-phenylmethyl)pyrazol-5-yl]pyridinium chloride (Compound 25)

Yield: 27%

IR (KBr, cm$^{-1}$): 3060, 2908, 1679, 1554.

$^1$H NMR (DMSO-d$_6$, 400 MHz) δ: 13.45 (1H, s), 9.35 (1H, s), 8.91 (1H, d), 8.80 (1H, d), 8.20 (1H, s), 8.14 (1H, t), 7.35–7.31 (5H, m), 6.74 (1H, s), 5.36 (2H, s), 4.07 (2H, s), 2.02–1.95 (9H, m), 1.62 (6H, s)

MASS (m/z): 427, 428, 429

EXAMPLE 27

1-(2-Phenyl-2-oxoethyl)-3-[{3-(3,5-dimethylpyrazol-1-yl)methyl}1-phenyl-pyrazol-5-yl]pyridinium bromide (Compound 26)

Yield: 47%

IR (KBr, cm$^{-1}$): 3410, 3035, 2943, 1693, 1500.

$^1$H NMR (DMSO-d$_6$, 400 MHz) δ: 9.19 (1H, s), 8.93–8.91 (1H, d), 8.25–8.23 (1H, d), 8.18–8.14 (1H, m), 8.07–8.05 (2H, m), 7.82–7.79 (1H, m), 7.69–7.64 (2H, m), 7.53–7.47 (3H, m), 7.40–7.37 (2H, m), 6.71 (1H, s), 6.40 (2H, s), 5.84–5.83 (1H, s), 5.28 (2H, s), 2.29 (3H, s), 2.08 (3H, s)

MASS (m/z): 448, 449

EXAMPLE 28

1-(2-(4-nitro-2-thienyl)-2-oxoethyl)-3-[(1-cyclohexyl-3-(3,5-dimethylpyrazol-1-yl)-methyl)pyrazol-5-yl]pyridinium bromide (Compound 27)

Yield: 56%

IR (KBr, cm$^{-1}$): 3421, 3032, 2935, 1688, 1541.

$^1$H NMR (DMSO-d$_6$, 400 MHz) δ: 9.30 (1H, d), 9.14 (1H, s), 9.04–9.02 (1H, d), 8.87–8.86 (1H, d), 8.79–8.77 (1H, d), 8.38–8.35 (1H, m), 6.46 (2H, s), 6.36 (1H, s), 5.82 (1H, s), 5.18 (2H, s), 4.15–4.10 (1H, m), 2.25 (3H, s), 2.07 (3H, s), 1.90–1.84 (4H, m), 1.81–1.77 (2H, d), 1.66–1.63 (1H, d), 1.38–1.19 (3H, m).

MASS (m/z): 505, 506, 507

EXAMPLE 29

1-(2-(4-Nitro-2-thienyl)-2-oxoethyl)-3[(3-(2-cyclohexylethyl)pyrazol-5-yl]pyridinium bromide (Compound 28)

Yield: 48%

IR (KBr, cm$^{-1}$): 3078, 3005, 1695, 1541, 1339

$^1$H NMR (DMSO-d$_6$, 400 MHz) δ: 13.24 (1H, s), 9.48 (1H, s), 9.30 (1H, s), 9.0 (1H, d), 8.87–8.84 (2H, m), 8.27 (1H, t), 6.76 (1H, s), 6.46 (2H, s), 2.69 (2H, t), 1.99–1.61 (5H, m), 1.58–1.52 (2H, q), 1.26–1.12 (4H, m), 0.96–0.87 (2H, m)

MASS (m/z): 425

EXAMPLE 30

1-(2-Thien-2'-yl-2-oxoethyl)-3-[(1-phenyl-3-phenoxymethyl)pyrazol-5-yl]pyridinium chloride (Compound 29)

Yield: 16%

IR (KBr, cm$^{-1}$): 3347, 3022, 2906, 1682, 1503

$^1$H NMR (DMSO-d$_6$, 400 MHz) δ: 9.3(1H,s), 9.0(1H,s), 8.29–8.24(4H,m), 7.6–7.3(8H,m), 7.0(3H,s), 6.97(1H,s), 6.38(2H,s), 5.2(2H,s)

MASS (m/z): 452,453,454

EXAMPLE 31

1-(2-(4-Nitro-2-thienyl)-2-oxoethyl)-3-[(1-phenyl-3-phenyl methyl)pyrazol-5-yl]pyridinium bromide (Compound 30)

Yield: 23%

IR (KBr, cm$^{-1}$): 3092,3003,2932,1687,1509

$^1$H NMR (DMSO-d$_6$, 400 MHz) δ: 9.298(1H,s), 9.16(1H,s), 8.917(1H,d), 8.85–8.84(1H,m), 8.54(1H,d),8.17–8.14(1H,m,), 7.50–7.45(3H,m), 7.39–7.31(6H,m), 7.25–7.22(1H,m), 6.7(1H,s), 6.357(2H,s), 4.0(2H,s)

MASS (m/z): 481,482

EXAMPLE 32

1-(2-Cyclopropylamino-2-oxoethyl)-3-[(3-phenoxymethyl)pyrazol-5-yl]pyridinium chloride (Compound 31)

Yield: 34%

IR (KBr, cm$^{-1}$): 3647,3420,3227,2958,1675

$^1$H NMR (DMSO-d$_6$, 400 MHz) δ: 13.82(1H,s), 9.46(1H,s), 8.98(1H,s), 8.87(1H,d), 8.77(1H,m) (1H,d), 8.207 (1H,t), 7.33(2H,t), 7.1(1H,s), 7.059(2H,d), 6.98(1H,t), 5.4(2H,s), 5.21(2H,s), 2.7–2.68(1H,m), 0.715–0.685(2H,m), 0.55–0.50 (2H,m)

MASS (m/z): 349,350,351

EXAMPLE 33

1-(2-Cyclopropylamino-2-oxoethyl)-3-[1(1-cyclohexyl-3-(3,5-dimethyl pyrazol-1-yl)methyl)pyrazole-5-yl]pyridinium chloride (Compound 32)

Yield: 41%

IR (KBr, cm$^{-1}$): 3425,3174,2938,1658,1500

$^1$H NMR (DMSO-d$_6$, 400 MHz) δ: 9.1(1H,s), 9.02(1H,d), 8.88(1H,d), 8.86(1H,d), 8.273(1H,t), 6.36–6.34(1H,s), 5.8 (1H,s), 5.4(2H,s), 5.18(2H,s), 4.13–4.079(1H,m), 2.7–2.68 (1H,m), 2.26(3H,s), 2.074(3H,s), 1.99–1.75(6H,m), 1.64–1.61(1H,m), 1.34–1.31(2H,m), 1.24–1.17(1H,m), 0.70–0.69(2H,m), 0.50–0.49(2H,m)

MASS (m/z): 433,434,435

EXAMPLE 34

1-(2-(5-Chloro-2-thienyl)-2-oxoethyl)-3-[(3-phenoxymethyl)pyrazol-5-yl]pyridinium bromide (Compound 33)
Yield: 74%
IR (KBr, cm$^{-1}$): 2853,2682,1674,1594
$^1$H NMR (DMSO-$d_6$, 400 MHz) δ: 13.8(1H,s),9.53(1H,s), 9.03(1H,d), 8.89(1H,d), 8.3–8.26(1H,m), 8.16(1H,d), 7.5 (1H), 7.33(2H,t), 7.08(3H,t), 6.98(1H,t), 6.38(2H,s), 5.2(2H, s)
MASS (m/z): 410,412,413

EXAMPLE 35

1-(2-Phenyl-2-oxoethyl)-3-[(1-phenyl-3-phenoxymethyl)pyrazol-5-yl]pyridinium chloride (Compound 34)
Yield: 25%
IR (KBr, cm$^{-1}$): 3020,2905,1701,1634,1595
$^1$H NMR (DMSO-$d_6$, 400 MHz) δ: 9.23(1H,s), 8.96(1H, d), 8.33(1H,d), 8.21(1H,t), 8.07(2H,d), 7.81(1H,t), 7.68(2H, t), 7.51–7.50(3H,m), 7.41(2H,d), 7.32(2H,t), 7.08–7.06(3H, m), 6.97(1H,t), 6.42(2H,s), 5.21(2H,s)
MASS (m/z): 446,447

EXAMPLE 36

1-(2-Thien-2'-yl-2-oxoethyl)-3-[(1-cyclohexyl-3-(3,5-dimethylpyrazol-1-yl)methyl)pyrazol-5-yl]pyridinium chloride (Compound 35)
Yield: 26%
IR (KBr, cm$^{-1}$): 3422,2937,1678,1505,1251
$^1$H NMR (DMSO-$d_6$, 400 MHz) δ: 9.17(1H,s), 9.05(1H, d), 8.76(1H,d), 8.35(1H,t), 8.25–8.24(2H,m), 7.42(1H,t), 6.41(2H,s), 6.36(1H,s), 5.85(1H,s), 5.18(2H,s),4.13–4.10 (1H,m), 2.25(3H,s), 2.06(3H,s), 1.99–1.86(4H,m), 1.83–1.76(2H,m), 1.66–1.63(1H,m), 1.35–1.25(2H,m), 1.22–1.16(1H,m)
MASS (m/z): 460,461,462

EXAMPLE 37

1-(2-cyclopropylamino-2-oxoeyhyl)-3-[(1-phenyl-3-phenoxymethyl)pyrazol-5-yl]pyridinium bromide (Compound 36)
Yield: 9%
IR (KBr, cm$^{-1}$): 3200,1682,1595
$^1$H NMR (DMSO-$d_6$, 400 MHz) δ: 9.29(1H,s),9.06(1H,s), 8.97(1H,d), 8.21(1H,d), 8.10(1H,t), 7.48(3H,s), 7.39–7.18 (5H,m), 7.14–7.07(2H,m), 6.97(1H,t), 5.43(2H,s), 5.20(2H, s),2.68–2.62(1H,m), 0.70–0.62(2H,m), 0.50–0.44(2H,m).
MASS (m/z): 425,426,427

EXAMPLE 38

1-(2-Thien-2'-yl-2-oxoethyl)-3-[1-phenyl-3-(2-cyclohexylethyl)pyrazol-5-yl]pyridinium bromide (Compound 37)
Yield: 31%
IR (KBr, cm$^{-1}$): 3423,3324,2922,1674,1506
$^1$H NMR (DMSO-$d_6$, 400 MHz) δ: 9.25(1H,s), 8.90(1H, d), 8.27–8.23(3H,m), 8.19–8.15(1H,m), 7.49–7.41(4H,m), 7.35(2H,d), 6.8(1H,s), 6.37(2H,s), 2.69(2H,t), 1.77(2H,d), 1.69–1.55(5H,m), 1.32(1H,m), 1.26–1.12(3H,m), 0.97–0.89 (2H,m).
MASS (m/z): 456,457,458

EXAMPLE 39

1-(2-Thien-2'-yl-2-oxoethyl)-3-[(1-cyclohexyl-3-phenoxymethyl)pyrazol-5-yl]pyridinium chloride (Compound 38)
Yield: 18%
IR (KBr, cm$^{-1}$): 3396,2934,1670,1638,1594
$^1$H NMR (DMSO-$d_6$, 400 MHz) δ: 9.25(1H,s), 9.10(1H, d), 8.82(1H,d), 8.39(1H,t), 8.26–8.25(2H,m), 7.43(1H,t), 7.30(2H,t), 7.04(2H,d), 6.95(1H,t), 6.75(1H,s), 6.46(2H,s), 5.09(2H,s), 4.20–4.15(1H,m), 1.93–1.77(6H,m), 1.67(1H, d), 1.36–1.20(3H,m).
MASS (m/z): 458,459,460

EXAMPLE 40

3-[(3-Phenylmethyl)pyrazol-5-yl]pyridine hydrochloride (Compound 39)
Yield:73%
IR (KBr, cm$^{-1}$): 3056,1611,1559
$^1$H NMR (DMSO-$d_6$, 400 MHz) δ: 9.18(1H,s), 8.73(2H, d), 7.93(1H,t), 7.35–7.22(5H,m), 6.77(1H,s), 4.04(2H,s)
MASS (m/z): 236,237

EXAMPLE 41

3-[(3-Phenoxymethyl)pyrazol-5-yl]pyridine hydrochloride (Compound 40)
Yield: 65%
IR (KBr, cm$^{-1}$): 3035,1601,1562
$^1$H NMR (DMSO-$d_6$, 400 MHz) δ: 9.25(1H,s), 8.77(2H, s), 7.97(1H,t), 7.32(2H,t), 7.12(1H,s), 7.05(2H,d), 6.97(1H, t), 5.17(2H,s)
MASS (m/z): 252,253,254

EXAMPLE 42

3-[(3,5-Dimethylpyrazol-1-yl-methyl)pyrazol-5-yl] pyridine (Compound 41)
Yield: 93%
IR (KBr, cm$^{-1}$): 3080,1559

$^1$H NMR (DMSO-d$_6$, 400 MHz) δ: 13.30(1H,bs), 8.96 (1H,s), 8.49(1H,s), 8.11(1H,d), 7.43(1H,bs), 6.63(1H,s), 5.81(1H,s), 5.17(2H,s), 2.28(3H,s), 2.07(3H,s)

MASS (m/z): 254,255,256

EXAMPLE 43

3-[3-(2-cyclohexylethyl)-pyrazol-5-yl]pyridine (Compound 42)

Yield: 76%

IR (KBr, cm$^{-1}$):

$^1$H NMR (DMSO-d$_6$, 400 MHz) δ: 12.73(1H,s), 8.98(1H, s), 8.46(1H,s), 8.11(1H,d), 7.46–7.38(1H,d), 6.57(1H,s), 2.63(2H,t), 1.75–1.60(5H,m), 1.56–1.50(2H,m), 1.25–1.08 (4H,m), 0.95–0.87(2H,m).

MASS (m/z): 256, 257, 258.

EXAMPLE 44

1-(2-Napthyl-2-oxo ethyl)-3[(3-phenoxymethyl) pyrazol-5-yl]pyridinium bromide (Compound 43)

Yield: 30%

IR (KBr, cm$^{-1}$): 3417, 2340, 1638, 1536, 1144

$^1$HNMR (DMSO-d6, 400 MHz) δ: 13.8 (1H, s), 9.58 (1H, s), 9.08–9.06 (1H,d), 8.95–8.93(1H, d), 8.85 (1H, s), 8.32 (1H, t), 8.25–8.23 (1H, d), 8.18–8.16 (1H, d), 8.10–8.05 (2H, m), 7.79–7.70 (2H, m), 7.33 (2H, t), 7.10 (1H, s), 7.06–7.04 (2H,d), 6.98 (1H, t), 6.63 (2H, s), 5.23 (2H, s)

MASS (m/z): 420, 421

EXAMPLE 45

1-(Phenylmethyl)-3[(3-phenyl methyl)pyrazol-5-yl]pyridinium chloride (Compound 44)

Yield: 31%

IR(KBr, cm$^{-1}$): 3051, 1523, 1466

$^1$HNMR (DMSO-d6, 400 MHz) δ: 13.48 (1H, s), 9.63 (1H, s), 9.05–9.03 (1H, d), 8.91–8.90 (1H, d) 8.15 (1H,t) 7.55 (2H, m), 7.45–7.43 (3H, m), 7.34–7.25 (5H,m) 6.79 (1H, s), 5.88 (2H, s), 4.06 (2H, s)

MASS (m/z): 326, 327, 328

EXAMPLE 46

1-(2-Thien-2'-yl-2-oxo ethyl)-3[(3-(-1-naphthyl)pyrazol-5-yl]pyridinium chloride (Compound 45)

Yield: 22%

IR (KBr, cm$^{-1}$): 3057, 1671, 1517

$^1$HNMR (DMSO-d6, 400 MHz) δ: 13.60 (1H, s), 9.40 (1H, s) 8.97–8.95 (1H, d), 8.86–8.85 (1H, d), 8.23–8.18 (3H, m), 8.10–8.08 (1H, d), 7.87–7.86 (1H, d), 7.55–7.44(4H, m), 7.40 (1H, t), 6.55–6.52 (1H, s), 6.40 (2H, s), 4.54 (2H, s)

MASS (m/z): 410, 411, 412

EXAMPLE 47

1-(2-Phenyl-2oxoethyl)-3[3(thienyl-2-yl-methyl) pyrazol-5-yl]pyridinium chloride (compound 46)

Yield: 22%

IR (KBr cm$^{-1}$): 3068, 1691, 1519

$^1$HNMR (DMSO-d6, 400 MHz) δ: 13.55 (1H, s), 9.50 (1H, s), 9.01 (1H, d), 8.87 (1H, d), 8.26 (1H, t) 8.07 (2H, m), 7.81 (1H, d), 7.68 (3H, t), 7.40 (2H, m), 6.78 (1H, s), 6.49 (2H, s) 4.30 (2H), s)

MASS (m/z): 360, 361

EXAMPLE 48

1-(2-(5-methyl-2-thienyl)-2-oxoethyl)-3-[3(2-phenyl ethyl)pyrazol-5-yl]pyridinium chloride (Compound 47)

Yield: 24%

IR (KBr cm$^{-1}$): 3068, 1661, 1450

$^1$HNMR (DMSO-d6, 400 MHz) δ: 13.33 (1H, s), 9.47 (1H, s), 8.97–8.95 (1H, d), 8.87–8.86 (1H, d), 8.26–8.22 (1H, t), 8.05–8.04 (1H, d), 7.31–7.14 (6H, m) 6.78 (1H, s), 6.34 (2H, s), 2.98 (4H, s), 2.59 (3H, s)

MASS (m/z): 388, 389, 390

EXAMPLE 49

1-(2-(5-Methyl 2-thienyl)-2-oxo ethyl)-3-[3-(3-phenoxy propyl)pyrazol-5-yl]pyridinium chloride (Compound 48)

Yield: 30%

IR (KBr cm$^{-1}$): 3057, 1665, 1452

$^1$HNMR (DMSO-d6, 400 MHz) δ: 13.34 (1H, s), 9.48 (1H, s), 8.99–8.97 (1H, d), 8.23(1H, t), 8.05–8.04 (1H, d), 7.28 (1H, t), 7.15–7.14 (1H, d), 6.94–6.92 (3H, d) 6.83(1H, s), 6.35 (2H, s), 4.02 (2H, t), 2.86 (2H, t), 2.27 (2H, t)

MASS (m/z): 418, 419, 420

EXAMPLE 50

1-(Isopropyl)-3[(3-phenylmethyl)pyrazol-5-yl]pyridinium bromide (Compound 49)

Yield: 15%

IR (KBr, cm$^{-1}$): 3418, 2364, 1648

$^1$HNMR (DMSO-d6, 400 MHz) δ: 9.43 (1H, s), 9.09–9.07 (1H, d), 8.88–8.86 (1H, d), 8.16 8.13 (1H, m), 7.36–7.14 (5H, m), 6.84 (1H, s), 4.06 (2H, s), 1.65–1.63 (6H, d)

MASS (m/z): 278, 279, 280

EXAMPLE 51

1-(2-(5-methyl-2-thienyl)-2-oxoethyl)-3-[(3-phenylthiomethyl)pyrazol-5-yl]pyridinium chloride (Compound 50)

Yield: 31%

IR(KBr cm$^{-1}$): 3365, 1650, 1452

$^1$HNMR (DMSO-d6, 400 MHz) δ: 13.58 (1H, s), 9.46 (1H, s), 8.98–8.96(1H, d), 8.87–8.85 (1H, d), 8.25–8.21 (1H, m), 8.04–8.03 (1H, d), 7.37–7.30 (5H, m), 7.15–7.14 (1H, d), 6.88 (1H, s), 6.32 (2H, s), 4.36 (2H, s), 2.59 (3H, s)

MASS (m/z): 406, 407, 408, 409

EXAMPLE 52

1-(2-Thien-2'-yl-2-oxoethyl)-3[(3-(N-methyl-indole-3-yl methyl)pyrazol-5-l]pyridinium chloride (compound 51)

Yield: 20%

IR (KBr cm$^{-1}$): 3070, 1669, 1410

$^1$HNMR (DMSO-d6, 400 MHz) δ: 9.32–9.30 (1H, m), 9.00–8.92 (2H, m), 8.77–8.76 (1H, d), 8.19–8.15 (2H, m), 8.10–8.07 (1H, m), 7.47–7.45 (1H, d), 7.39–7.35 (3H, m) 7.19–7.10 (2H, m) 7.03–7.00 (1H, t), 6.34 (2H, s), 4.22 (1H, s), 3.79 (3H, s)

MASS (m/z): 413

EXAMPLE 53

1-(2-Napthyl-2-oxo-ethyl)-3[(3-methyl)pyrazol-5-yl]pyridinium bromide (Compound 52)

Yield: 38%

IR (KBr, cm$^{-1}$): 3066, 1675, 1518

$^1$HNMR (DMSO-d6, 400 MHz) δ: 13.25 (1H, s), 9.53 (1H, s) 9.02–9.0 (1H, d), 8.92–8.91 (1H, d), 8.84 (1H, s), 8.32–8.04 (5H, m), 7.79–7.70 (2H, m), 6.75 (1H, s), 6.63 (2H, s), 2.33 (3H, s)

MASS (m/z): 328, 329, 330

EXAMPLE 54

1-(2-(1,4 benzodioxane-6-yl-amino-2-oxoethyl)-3 [(3-phenylmethyl)pyrazol-5-yl]pyridinium chloride (Compound 53)

Yield: 32%

IR (KBr, cm$^{-1}$): 3445, 3068, 1678

$^1$HNMR (DMSO-d6, 400 MHz) δ: 13.45 (1H, s), 10.61 (1H, s), 9.47 (1H, s), 8.97–8.95 (1H, d), 8.91–8.89 (1H, d), 8.2 (1H, t), 7.34–7.19 (6H, m), 6.99–6.97 (1H, d), 6.84–6.82 (1H, d), 6.72 (1H, s), 5.61 (2H, s), 4.21 (4H, s), 4.06 (2H, s)

MASS (m/z): 427, 428, 429

EXAMPLE 55

1-(2-Thien-2-yl-2-oxo ethyl)-3[(3-phenyl)pyrazol-5-yl]-5-bromopyridinium chloride (Compound 54)

Yield: 31%

IR (KBr, cm$^{-1}$)

$^1$HNMR (DMSO-d6, 400 MHz) δ: 9.63 (1H, s), 9.36 (1H, s), 9.33 (1H, s), 8.27–8.24 (2H, m), 7.81–7.79 (2H, d), 7.57–7.52 (3H, m), 7.46–7.42 (2H, m), 6.40 (2H, s)

MASS (m/z): 426, 427, 428

EXAMPLE 56

1-(2-Thien-2-yl)-2-oxoethyl)-3[(3-phenyl)pyrazol-5-yl]quinolinium chloride (Compound 55)

Yield: 26%

IR (KBr, cm$^{-1}$)

$^1$HNMR (DMSO-d6, 400 MHz) δ: 10.18 (1H, s), 9.81 (1H, s) 8.45–8.40 (3H, m), 8.29–8.28 (1H, d), 8.21 (1H, t), 8.08 (1H, t) 7.87–7.85 (2H, d), 7.57–7.55 (3H, m), 7.50–7.45 (2H, m), 6.96 (2H, s)

MASS (m/z): 396, 397, 398

EXAMPLE 57

3-[(3-phenyl)pyrazol-5-yl)]quinoline (Compound 56)

Yield: 70%

$^1$HNMR (DMSO-d6, 400 MHz) δ: 9.45 (1H, bs), 8.75 (1H, s), 8.05 (2H, d), 7.87 (2H, bs), 7.77 (1H, t), 7.65 (1H, t), 7.55–7.45 (3H, m), 7.39 (1H, bs)

MASS (m/z): 272 (M$^+$+1)

Cosmetic Preparation

The preparation for use in cosmetic application may contain one or more concentration of the compound in a cosmetically acceptable vehicle. The amount of the compound of invention will preferably range between 0.005 to 50% by weight (unless otherwise noted, all fraction amounts are expressed in weight percent), more preferably between 0.20% and 5.0% w/w. The composition should be applied based on the requirement to an affected area.

Suitable vehicles or carriers for storage and/or delivery of the novel compound of this invention may be provided in lotion, liquid, ointment, gels, creams, spray, poultice or other forms, and will preferably have a lipophilic, hydrophilic or amphiphilic character. Suitable carriers include petrolatum, triglycerides, various esters, fatty alcohols, fatty acid, alkylene glycols, and ethanol, of which polyethylene glycol and polypropylene glycol are most preferred; if desired, compatible combinations of these vehicles are also suitable.

Further more the vehicles are present as needed for the desired delivery system. The vehicles or carriers can also have additional agents according to conventional practice. For example, the final composition may contain various emollients, emulsifiers, alcohols, colorants, fragrances, thickeners (such as xanthan gum), preservatives, humectants, surfactants (anionic, cationic, nonionic, amphoteric alone or in combinations), agents which modify skin differentiation and/or proliferation and/or pigmentation, antiparasitic agents, dispersants, opacifier, gelling agent, hydrating agent, additional antioxidants, the typical botanical extracts such as those derived from aloe, citrus fruits, Witch Hazel, chamomile, and other like e.g., those having an astringent, antiseptic, sunscreens or suntan effects, skin toners, silicones, exfoliating agents, keratolytic agnets, retinoids, skin penetration enhancers, vitamins, thrombolytic agents, anti-clotting agents, capillary protectants, hormones, antibacterial agents, antiviral agents, steroidal anti-inflammatory agents, anaesthetics, anti-seborrhoeic agents, anti-dandruff agents, anti-acne agents, anti-free radical agents, analgesics, lipophilic compounds, antihistamine agents, insect repellants, skin cooling compounds, lubricants, anti-fungal agents or mixtures thereof. The composition may likewise include a penetration enhancer such as, but not limited to, Oleic acid, DMSO (dimethyl sulfoxide), alcohols, N-methylpyrolidone, dimethyl isosorbide. It may also include one or more additional active ingredients such as anti-inflammatory agents, antibiotic, astringents, growth factors, tocopherols, retinols, free radical scavengers.

The following non-limiting examples are for cosmetic composition according to the instant invention.

EXAMPLE 58

| | |
|---|---|
| Compound of invention | 0.3% w/w |
| Oleic acid | 10.0% w/w |
| Propylene Glycol | 70.0% w/w |
| Tween 80 | 0.1% w/w |
| Absolute ethanol. qs | 100.0% w/w |

EXAMPLE 59

| | |
|---|---|
| Compound of invention | 0.3% w/w |
| Oleic acid | 10.0% w/w |
| Colliodal silicon Dioxide | 6.0% w/w |
| Tween 80 | 0.1% w/w |
| Caprylic capric Triglyceride qs | 100.0% w/w |

A cosmetically acceptable organic fatty acid can optionally be present independently in the composition in an amount, preferably a bioactively effective amount, of 0.1% to 10.0%; the addition of fatty acid is a preferred ingredient.

The effect of the compound of invention synergistically improves when combined with a humectant, an emollient, additional antioxidants or an anti-inflammatory agent.

EXAMPLE 60

| | |
|---|---|
| Compound of invention | 0.4% w/w |
| Fatty acid | 4.0% w/w |
| Mineral oil | 5.0% w/w |
| Isocetyl stearate | 1.0% w/w |
| Antioxidant | 0.05% w/w |
| Xanthan gum | 0.2% w/w |
| Glycerol | 50.0% w/w |
| Diazolidinyl urea | 0.2% w/w |
| Lemon peel Extract | 0.02% w/w |
| Alcohol | 2.0% w/w |
| Purified water | 100.0% w/w |

The addition of humectants and emollients to the antioxidant composition is expected to aid in the rehydration and maintenance of hydration of the skin under consideration. Improved hydration of the skin is believed to both increase the absorbence of the free radical scavenger by the skin and helps in the delivery of the free radical scavenger to the active site.

Examples of the emollients which can be used are: mineral oil, petrolatum, paraffin, ceresin, ozokerite, microcrystalline wax, perhydrosqualene dimethyl polysiloxanes, methylphenyl polysiloxanes, silicone, silicone-glycol copolymers, triglyceride esters, acetylated monoglycerides, ethoxylated glycerides, alkyl esters of fatty acids, fatty acids and alcohols, lanolin and lanolin derivatives, polyhydric alcohol esters, sterols, beeswax derivatives, polyhydric alcohols and polyethers, and amides of fatty acids. Although various emollients known in the art would be useful in the present invention, the preferred emollient is silicone.

Humectants known in the art to increase skin hydration when applied topically, such as polyhydric alcohols, are appropriate. Examples of suitable humectants are: glycerin, propylene glycol, butylene glycol, diglycerol, or ester derivatives thereof. However, the preferred humectant is glycerin.

The topical preparation of the present invention may contain a single antioxidant, apart from the compound of the invention or a combination of antioxidants, thus an antioxidant blend. The term "antioxidant" as used herein is intended to encompass both a single antioxidant as well as an antioxidant blend. The antioxidant may also be incorporated into various vehicles to facilitate topical application.

In order to obtain elegant, topical compositions in the form of cream, emulsions, lotions or gels, such compositions may include from about 0.001 wt % to about 50 wt % of an antioxidant.

The topical compositions of the present invention can be made as lotions and creams.

The free radical scavenger can be combined with most emulsifiers that are used to make lotions, creams and other suitable topical vehicles. The emulsifiers can be cationic, anionic, nonionic, amphoteric, or a combination thereof. Nonionic emulsifiers are preferred. Exemplary nonionic emulsifiers are commercially available sorbitans, alkoxylated fatty alcohols and alkyl polyglycosides. Anionic emulsifiers may include soaps, alkyl sulfates, monoalkyl and dialkyl phosphates, alkyl sulphonates and acyl isothionates, an amphoteric emulsifier that may be used is lactamidopropyl trimonium chloride.

Suitable vehicles for composition of the present invention may also contain thickeners. Examples of suitable thickeners include cellulose derivatives, such as hydroxyethyl cellulose and hydroxypropyl cellulose, as well as polyacrylic acid polymers.

Examples of preservatives that are suitable for use with the compositions include alkanols, especially ethanol and benzyl alcohol; parabens; sorbates; urea derivatives; and, isothiazolinones.

Lotions or creams according to the present invention can be made using conventional homogenization methods known to those skilled in the art. It is also possible to use a process of microfluidization that involves co-mixing the aqueous phase and the oil phase of such creams and lotions in a high-pressure homogenizer that reduces the emulsion particle size dramatically to about several microns of those in creams and lotions prepared without applying high pressure. Microfluidization allows one to prepare elegant stable creams and lotions containing effective amounts of the compound without the use of traditional emulsifiers and surfactants.

The topical compositions of the present invention can also be formulated as a micro-emulsion, which is a subcategory of emulsions, oils that may be used are mineral oil and silicone oil. Examples of alcohols that may be used are cetyl alcohol, isostearyl alcohol, stearyl alcohol, dodecanol and dodecenol. Nonionic surfactants may be fatty esters, esters of fatty alcohols or ethoxylated alcohols. Examples of nonionic surfactants are polyethylene glycol, isopropyl myristate, cetyl isooctadecanoate, polypropylene glycols, sorbitants and isopropyl oleate.

EXAMPLE 61

| Compound of invention | 0.2% w/w |
|---|---|
| Fatty acid | 1.5% w/w |
| Surfactant | 3.0% w/w |
| Cosolvent | 70.0% w/w |
| Purified water | (qs) 100.0% w/w |

The topical compositions of the invention can be formulated as oil-in-water or water-in-oil emulsions. The compositions can also be in the form of a multiphase emulsion, such as a water-in-oil-in-water type emulsion The compositions of the invention can also be made as a liposomal formulation. In such compositions, compound solution can be entrapped inside the liposomal vesicles with the shell of the liposome being a phospholipid or other suitable lipids (e.g. skin lipids). To form a topical composition, the liposomes can then be added to any carrier system described above according, to the preparation modes, uses and compositions of topical liposomes.

EXAMPLE 62

| Compound of invention | 0.4% w/w |
|---|---|
| Phospholipid | 6.0% w/w |
| Antioxidants | 05% w/w |
| Ethanol | 15.0% w/w |
| Hydrophilic medium | (qs) 100.0% w/w |

Solutions of compound and antioxidants can also be entrapped in polymeric vesicles with a shell comprising of a suitable polymeric material, such as gelatin, cross-linked gelatin, polyamide, polyacrylates and the like to form a vesicle that is then incorporated into the topical composition.

The composition according to the instant invention can be used for one or more of the following cosmetic applications, namely (a) reversing and preventing wrinkles b) reversing and preventing fine lines (c) promoting epidermal growth (d) photo protection (e) reversing and preventing skin discoloration (f) reversing and preventing age spots (g) conditioning and preventing dryness (h) reversing and preventing stretch marks (i) reversing and preventing blemishes (j) skin care/skin conditioning (k) reversing and preventing senile xerosis (l) conditioning and preventing sun burns (m) preventing and reversing the loss of collagen (n) improving skin texture (o) improving skin tone (p) enhancing skin thickness (q) decreasing pore size (r) restoring skin luster (s) minimizing signs of fatigue (t) reducing acne, (u) treatment of Telangiectasia and (v) improving asthetic appearance of hair and nail.

Pharmaceutical Compositions

Pharmaceutical compositions effective for scavenging free radicals an/or inhibiting AGE may be prepared with a pharmaceutically effective quantity of compounds of general formula I, individually or in combination. The amount of the compound of invention will preferably range between 0.00001 to 90% by weight. The following pharmaceutical formulations suggested are by way of example alone and in no way restrict the scope of the invention.

Oral Formulations

Oral formulations may be administered as solid dosage forms for example pellets, powders, sachets or discreet units such as tablets or capsules and like. Other orally administered pharmaceutical preparations include monophasic and biphasic liquid dosage forms either in ready to use form or forms suitable for reconstitution such as mixtures, syrups, suspensions or emulsions. The preparations in addition may contain diluents, dispersing agents, buffers, stabilizers, solubilizers, surfactants, preservatives, chelating agents and/or other pharmaceutical additives as are used. Aqueous or non aqueous vehicle or their combination may be used and if desired may contain suitable sweetener, flavoring agent or similar substances. In case of suspension or emulsion a suitable thickening agent or suspending agent or emulsifying agent may be present in addition. Alternatively, the compounds may be administered as such in their pure form unassociated with other additives for example as capsules or sachets. It may also be administered with a vehicle. Pharmaceutical preparations can have a slow, delayed or controlled release of active ingredients as is provided by a matrix or diffusion controlled system.

When the present invention or its salts or suitable complexes is presented as a discreet unit dosage form like tablet, it may contain in addition medically inert excipients as are used in the art. Diluents such as starch, lactose, dicalcium phosphate, talc, magnesium stearate, polymeric substances like methyl cellulose, fatty acids and derivatives, sodium starch glycollate, etc. may also be used.

EXAMPLE 63

| Preparation of oral dosage form: | |
|---|---|
| A typical tablet can have the following composition: | |
| Active ingredient of general formula I | an effective amount |
| Lactose | 100 mg |
| Microcrystaline Cellulose | 51 mg |
| Starch | 60 mg |
| Polyvinyl pyrolidone (K-30) | 2 mg |
| Talc | 1.5 mg |
| Magnesium Stearate | 1.0 mg |
| OR | |
| Active ingredient of general formula I | an effective amount |
| Lactose | 130 mg |
| Starch | 75 mg |
| Polyvinyl pyrolidone (K-30) | 2 mg |
| Talc | 1.5 mg |
| Magnesium Stearate | 1.0 mg |

Parenteral Formulations

For parenteral administration, the compounds or their salts or suitable complexes thereof may be present in a sterile vehicle which may be an aqueous or non aqueous vehicle or a combination thereof. The examples of vehicles are water, ethyl oleate, oils and derivatives of polyols, glycols and their derivatives. It may contain additives common in injectable preparations like stabilizers, solubilizers, pH modifiers, buffers, antioxidants, cosolvents, complexing agents, tonicity modifiers, etc.

Some suitable additives are for example tartrate, citrate or similar buffers, alcohol, sodium chloride, dextrose and high molecular weight polymers. Another alternative is sterile powder reconstitution. The compound may be administered in the form of injection for more than once daily administration, or intravenous infusion/drip or suitable depot preparation.

EXAMPLE 64

| Preparation for parenteral administration: | |
|---|---|
| Active ingredient of general formula I | an effective amount |
| Polethylene glycol (400) | 20% w/v |
| Sodium metabisulphite | 0.01% w/v |
| Isotonic saline/WFI | q.s. to 100% |

Other Formulations.

For the dermatological application and for the discoloration of teeth; the recommended formulations are lotions, oral rinse and toothpaste containing appropriate amount of the compounds of the general formula I.

The above examples are presented by way of illustration alone and in no way limit the scope of the invention.

What is claimed is:

1. A compound represented by formula (I) or a pharmaceutically or cosmetically acceptable salt thereof

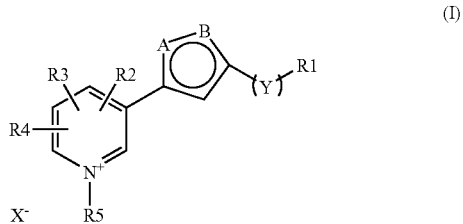

(I)

wherein, $R_1$ is hydrogen, dimethyl pyrazolyl, or selected from the group consisting of linear or branched ($C_1$–$C_{12}$) alkyl, ($C_2$–$C_{12}$) alkenyl, ($C_3$–$C_7$) cycloalkyl, ($C_5$–$C_7$) cycloalkenyl, bicycloalkyl, bicycloalkenyl, aryl, aralkyl, and is optionally substituted, wherein the substituents are selected from a first group consisting of halogen, hydroxy, nitro, cyano, amino, oxo and oxime, or from a second group consisting of linear or branched ($C_1$–$C_8$) alkyl, ($C_3$–$C_7$) cycloalkyl, alkylcycloalkyl, perhaloalkyl, perhalocycloalkyl, aryl, aralkyl, alkylaryl, aralkoxylalkyl, perhaloaryl, acyl, alkoxyalkyl, and thioalkyl, wherein the substitutents from said second group are optionally substituted by $R_{10}$ and are optionally and independently bridged by —(CO)O—, —(CO)NH—, —NH—, —$NR_8$—, —O—, —S—, —(SO)—, —($SO_2$)—, —($SO_2$)NH—, or —NH(CO)—;

Y is selected from the group consisting of null, ($C_1$–$C_{12}$) alkylene-Z or ($C_2$–$C_{12}$) alkylene, wherein Z is selected from sulfur, oxygen or nitrogen;

A and B are independently selected from N, NH, or $NR_6$ to form a heteroaromatic ring system;

$R_2$, $R_3$ and $R_4$ are independently selected from a first group consisting of hydrogen, halogen, $NO_2$, N=C ($R_8$)($R_9$), —$NR_8R_9$, —$OR_8$, perhaloalkyl, —(CO) $NR_8R_9$, —(CO)$R_8$, —(CO)$OR_8$, —O(CO)$R_8$, —NH (CO)$R_8$ or from a second group consisting of linear or branched ($C_1$–$C_{12}$) alkyl, ($C_2$–$C_{12}$)alkenyl, ($C_3$–$C_7$) cycloalkyl, ($C_5$–$C_7$)cycloalkenyl, bicycloalkyl, bicycloalkenyl, aryl, aralkyl, wherein one or more members of said second group when present are optionally substituted by $R_{10}$;

$R_5$ is selected from the group consisting of $CH_2$—C(O)-(thienyl), $CH_2$—C(O)-(methylthienyl); linear or branched ($C_3$–$C_{12}$)alkyl, ($C_2$–$C_{12}$)alkenyl, ($C_3$–$C_7$)cycloalkyl, ($C_5$–$C_7$)cycloalkenyl, bicycloalkyl; $CH_2$(CO) $R_7$, $CH_2$(CO)$NHR_8$, $CH_2$(CO)$NR_8R_9$, and $CH_2$(CO) $OR_7$ which are optionally substituted by $R_{10}$;

$R_6$ and $R_7$ are independently selected from the group consisting of linear or branched ($C_1$–$C_8$) alkyl, ($C_3$–$C_7$) cycloalkyl, alkylcycloalkyl, perhaloalkyl, perhalocycloalkyl, aryl, aralkyl, alkylaryl, aralkoxylalkyl, perhaloaryl, acyl, benzoyl, alkoxyalkyl, and thioalkyl, wherein members of said group are optionally substituted by $R_{10}$;

$R_8$ and $R_9$ are independently selected from the group consisting of linear or branched ($C_1$–$C_{12}$)alkyl, alkoxyaryl, alkoxyalkyl, alkoxycycloalkyl, perhaloalkyl, ($C_2$–$C_{12}$)alkenyl, ($C_3$–$C_7$)cycloalkyl, perhalocycloalkyl, ($C_5$–$C_7$)cycloalkenyl, bicycloalkyl, adamantyl, bicycloalkenyl, aryl, aralkyl, perhaloaryl, wherein members of said group are optionally substituted by $R_{10}$;

$R_{10}$ is selected from halogen, hydroxy, nitro, cyano, amino, oxo, perhaloalkyl ($C_1$–$C_6$), or oxime;

X is selected from the group consisting of a halide ion, acetate ion, perchlorate ion, sulfonate ion, oxalate ion, citrate ion, tosylate ion, maleate ion, mesylate ion, carbonate ion, sulfite ion, phosphoric hydrogen ion, phosphonate ion, phosphate ion, $BF_4^-$ and $PF_6^-$ Provided that;

"aryl" represents an aromatic carbocyclic group with at least one ring having a conjugated π-electron system, and containing up to two conjugated or fused ring systems.

2. The compound as claimed in claim 1, wherein said pharmaceutically or cosmetically acceptable salt is a salt of a carboxylic acid selected from an alkali metal salt and an alkaline earth metal salt; a salt of an organic base selected from lysine, arginine, guanidine, diethanolamine and choline; an ammonium or substituted ammonium salt; an aluminium salt; or an acid addition salt selected from the group consisting of a sulfate, nitrate, phosphate, perchlorate, borate, hydrohalide, acetate, tartrate, maleate, citrate, succinate, palmoate, methanesulfonate, benzoate, salicylate, hydroxynaphthoate, benzensulfonate, ascorbate, glycerophosphate and ketoglutarate.

3. A compound as claimed in claim 1, wherein $R_1$ is a substituted or unsubstituted group selected from linear or branched ($C_1$–$C_{12}$)alkyl, ($C_3$–$C_7$)cycloalkyl, and aryl.

4. A compound as claimed in claim 1, wherein Y is selected from the group consisting of null, ($C_1$–$C_8$) alkylene-Z and ($C_1$–$C_8$) alkylene, wherein Z is selected from sulfur, oxygen or nitrogen.

5. A compound as claimed in claim 1, wherein A and B are independently selected from NH and $NR_6$.

6. A compound as claimed in claim 1, wherein $R_2$, $R_3$ and $R_4$ are independently selected from the group consisting of hydrogen, halogen, $NO_2$ and perhaloalkyl.

7. A compound as claimed in claim 1, wherein $R_5$ is selected from the group consisting of $CH_2$—C(O)-(thienyl), $CH_2$—C(O)-(methylthienyl), $CH_2(CO)R_7$ and $CH_2(CO)NHR_8$, optionally substituted by $R_{10}$.

8. A compound as claimed in claim 1, wherein X is halide.

9. A compound selected from the group consisting of the following compounds, or a pharmaceutically acceptable salt thereof:

1-(2-thien-2'-yl-2-oxoethyl)-3-[(3-phenyl methyl) pyrazol-5-yl] pyridinium bromide;
1-(2-thien-2'-yl-2-oxoethyl)-3-[3-{1-(3,5-dimethylpyrazol-1-yl) methyl}pyrazol-5-yl] pyridinium bromide;
1-[2-(cyclopropylamino)-2-oxoethyl]3-[3-{(3,5-dimethyl pyrazol-1-yl) methyl}-pyrazol-5-yl]-pyridinium bromide;
1-{2-(4-nitro-2-thienyl)-2-oxoethyl}-3-[3{(3,5-dimethylpyrazol-1-yl) methyl}-pyrazol-5-yl]-pyridinium bromide;
1-(2-cyclopropylamino-2-oxoethyl)-3[(3-phenylmethyl) pyrazol-5-yl] pyridinium chloride;
1-(2-thien-2'-yl-2-oxoethyl)-3-[(1-phenyl-3-phenylmethyl) pyrazol-5-yl]-pyridinium chloride;
1-(2-(5-methyl-2-thienyl)-2-oxoethyl)-3-[(3-phenylmethyl) pyrazol-5-yl] pyridinium chloride;
1-(2-thien-2'-yl-2-oxoethyl) 3-[1-phenyl,3-{(3,5-dimethyl pyrazol-1-yl) methyl)} pyrazol-5-yl]-pyridinium chloride;
1-(2-phenyl-2-oxoethyl)-3-[(3-phenylmethyl) pyrazol-5-yl]-pyridinium bromide;
1-(2-cyclopropylamino-2-oxoethyl) 3-[(1-phenyl-3-phenylmethyl) pyrazol-5-yl]-pyridinium chloride;
1-(2-phenyl-2-oxoethyl)-3-[(3-(3,5-dimethylpyrazol-1-yl) methyl) pyrazol-5-yl]-pyridinium chloride;
1-(2-(5-methyl-2-thienyl)-2-oxoethyl)-3-[(3,-(3,5-dimethyl pyrazol-1-yl) methyl) pyrazol-5-yl] pyridinium chloride;
1-(2-phenyl-2-oxoethyl)-3[(1-phenyl-3-phenylmethyl) pyrazol-5-yl] pyridinium chloride;
1-(2-(5-methyl-2-thienyl)-2-oxoethyl)-3-[(3(2-cyclohexyl ethyl)pyrazol-5-yl] pyridinium chloride;
1-(2-cyclopropylamino-2-oxoethyl)-3-[(3-(2-cyclohexylethyl) pyrazol-5-yl] pyridinium chloride;
1-(2-phenyl-2-oxoethyl)-3-[(3-(2-cyclohexylethyl) pyrazol-5-yl] pyridinium chloride;
1-(2-cyclopropylamino-2-oxoethyl)-3-[(1-cyclohexyl-3-phenylmethyl) pyrazol-5-yl] pyridinium chloride;
1-(2-thien-2'-yl-2-oxoethyl)-3-[(3-phenoxymethyl) pyrazol-5-yl] pyridinium chloride;
1-[2-(1-adamantylamino)-2-oxoethyl]-3-[(3-phenylmethyl) pyrazol-5-yl] pyridinium chloride;
1-(2-phenyl-2-oxoethyl)-3-[{3-(3,5-dimethylpyrazol-1-yl)methyl)} 1-phenyl-pyrazol-5-yl] pyridinium bromide;
1-(2-(4-nitro-2-thienyl)-2-oxoethyl)-3-[(1-cyclohexyl-3-(3,5-dimethylpyrazol-1-yl)-methyl) pyrazol-5-yl] pyridinium bromide;
1-(2-(4-nitro-2-thienyl)-2-oxoethyl)-3[(3-(2-cyclohexylethyl)pyrazol-5-yl] pyridinium bromide;
1-(2-thien-2'-yl-2-oxoethyl)-3-[(1-phenyl-3-phenoxymethyl) pyrazol-5-yl] pyridinium chloride;
1-(2-(4-nitro-2-thienyl)-2-oxoethyl)-3-[(1-phenyl-3-phenylmethyl) pyrazol-5-yl] pyridinium bromide;
1-(2-cyclopropylamino-2-oxoethyl)-3-[(3-phenoxymethyl) pyrazol-5-yl] pyridinium chloride;
1-(2-cyclopropylamino-2-oxoethyl)-3-[(1-cyclohexyl-3-(3,5-dimethyl pyrazol-1-yl) methyl)pyrazol-5-yl] pyridinium chloride;
1-(2-(5-chloro-2-thienyl)-2-oxoethyl)-3-[(3-phenoxymethyl) pyrazol-5-yl] pyridinium bromide;
1-(2-phenyl-2-oxoethyl)-3-[(1-phenyl-3-phenoxymethyl) pyrazol-5-yl] pyridinium chloride;
1-(2-thien-2'-yl-2-oxoethyl)-3-[(1-cyclohexyl-3-(3,5-dimethylpyrazol-1-yl-methyl)pyrazol-5-yl] pyridinium chloride;
1-(2-cyclopropylamino-2-oxoethyl)-3-[(1-phenyl-3-phenoxymethyl) pyrazol-5-yl] pyridinium chloride;
1-(2-thien-2'-yl-2-oxoethyl)-3-[(1-phenyl-3-(2-cyclohexylethyl) pyrazol-5-yl] pyridinium chloride;
1-(2-thien-2'-yl-2-oxoethyl)-3-[(1-cyclohexyl-3-phenoxymethyl) pyrazol-5-yl] pyridinium chloride;
1-(2-napthyl-2-oxoethyl)-3[(3-phenoxymethyl)pyrazol-5-yl] pyridinium bromide;
1-(phenylmethyl)-3[(3-phenylmethyl)pyrazol-5-yl] pyridinium chloride;
1-(2-thien-2'-yl-2-oxoethyl)-3[(3(-1-naphthyl)pyrazol-5-yl] pyridinium chloride;
1-(2-(5-methyl-2-thienyl)-2-oxoethyl)-3-[3(2-phenylethyl) pyrazol-5-yl] pyridinium chloride;
1-(2-(5-methyl 2-thienyl)-2-oxoethyl)-3-[3-(3-phenoxy propyl)pyrazol-5-yl] pyridinium chloride;
1-(isopropyl)-3[(3-phenylmethyl)pyrazol-5-yl] pyridinium bromide;
1-(2-(5-methyl-2-thienyl)-2-oxoethyl)-3-[(3-thiophenylmethyl)pyrazol-5-yl] pyridinium chloride;
1-(2-napthyl-2-oxo-ethyl)-3[(3-methyl)pyrazol-5-yl] pyridinium bromide;
1-(2-thien-2'-yl)-2-oxoethyl)-3[(3-phenyl)pyrazol-5-yl]-5 bromo pyridinium chloride; and
1-(2-thien-2'-yl-2-oxoethyl)-3-[3 {(3,5-dimethylpyrazol-1-yl) methyl-1-(2-pyridyl)}pyrazol-5-yl]pyridinium bromide.

10. A pharmaceutical composition comprising a pharmaceutically effective amount of one or more compounds of general formula (I), as defined in claim 1 or a pharmaceutically acceptable salt thereof in admixture with a pharmaceutically acceptable carrier, diluent, solvent or excipient.

11. A pharmaceutical composition as claimed in claim 10, in the form of an oral formulation.

12. A pharmaceutical composition as claimed in claim 10, wherein said acceptable carrier, diluent, solvent or excipient is selected from the group consisting of starch, lactose, polyvinyl pyrolidone (K-30), talc and magnesium stearate.

13. A pharmaceutical composition as claimed in claim 10 in the form of a parenteral formulation.

14. The compound as claimed in claim 1, wherein one or more aryl groups when present are optionally substituted with F, Cl, Br, I, N, S, O, or straight chain or branched $C_1$–$C_6$ alkyl.

15. A pharmaceutical composition comprising the compound as defined in claim 9 or a pharmaceutically acceptable salt thereof in admixture with a pharmaceutically acceptable diluent, carrier, solvent or excipient.

* * * * *